(12) United States Patent
Ianiro et al.

(10) Patent No.: US 9,421,189 B2
(45) Date of Patent: *Aug. 23, 2016

(54) METHOD OF PREPARING A MUSCADINE POMACE EXTRACT

(71) Applicant: Shaklee Corporation, Pleasanton, CA (US)

(72) Inventors: Teodoro T. Ianiro, Concord, CA (US); Laurel A. Fisher, San Francisco, CA (US); William J. Mergens, West Palm Beach, CA (US)

(73) Assignee: Shaklee Corporation, Pleasanton, CA (US)

( * ) Notice: Subject to any disclaimer, the term of this patent is extended or adjusted under 35 U.S.C. 154(b) by 565 days.

This patent is subject to a terminal disclaimer.

(21) Appl. No.: 13/942,619

(22) Filed: Jul. 15, 2013

(65) Prior Publication Data

US 2013/0303603 A1 Nov. 14, 2013

Related U.S. Application Data

(63) Continuation of application No. 13/056,559, filed as application No. PCT/US2009/052346 on Jul. 31, 2009, now Pat. No. 8,512,771.

(60) Provisional application No. 61/085,371, filed on Jul. 31, 2008.

(51) Int. Cl.
| | |
|---|---|
| *A61K 36/87* | (2006.01) |
| *A61K 31/366* | (2006.01) |
| *A23L 1/30* | (2006.01) |
| *A61K 36/704* | (2006.01) |
| *A23L 2/52* | (2006.01) |
| *A61K 31/05* | (2006.01) |

(52) U.S. Cl.
CPC ............ *A61K 31/366* (2013.01); *A23L 1/3002* (2013.01); *A23L 2/52* (2013.01); *A61K 31/05* (2013.01); *A61K 36/704* (2013.01); *A61K 36/87* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,190,716 B1 | 2/2001 | Galbreath | |
| 6,638,545 B1 | 10/2003 | Rombi | |
| 8,017,147 B2 | 9/2011 | Mazed et al. | |
| 8,075,929 B2 | 12/2011 | Shrikhande et al. | |
| 8,114,445 B2 | 2/2012 | Hastings | |
| 8,173,181 B2 | 5/2012 | Ferguson et al. | |
| 8,182,849 B2 | 5/2012 | Endo et al. | |
| 8,512,771 B2 * | 8/2013 | Ianiro .................. | A23L 1/3002 424/766 |
| 8,568,804 B2 * | 10/2013 | Fisher .................. | A23L 1/3002 424/766 |
| 8,911,804 B2 * | 12/2014 | Fisher .................. | A23L 1/3002 424/766 |
| 9,132,162 B2 * | 9/2015 | Fisher .................. | A61K 36/87 |
| 9,173,916 B2 * | 11/2015 | Ianiro .................. | A61K 36/87 |
| 2004/0234671 A1 | 11/2004 | Ector et al. | |
| 2005/0158376 A1 | 7/2005 | Sardi et al. | |
| 2006/0024392 A1 | 2/2006 | Magnuson et al. | |
| 2006/0121137 A1 | 6/2006 | Hartle et al. | |
| 2006/0277887 A1 | 12/2006 | Dalton et al. | |
| 2007/0003644 A1 | 1/2007 | Randhava et al. | |
| 2009/0176718 A1 | 7/2009 | Ribnicky et al. | |
| 2010/0004344 A1 | 1/2010 | Dallas | |
| 2011/0177182 A1 | 7/2011 | Ianiro et al. | |
| 2011/0177183 A1 | 7/2011 | Ianiro et al. | |

FOREIGN PATENT DOCUMENTS

| | | |
|---|---|---|
| CN | 1343100 A | 4/2002 |
| CN | 1698733 A | 11/2005 |
| JP | 2002293736 A | 10/2002 |
| WO | WO 98/17250 A1 | 4/1998 |
| WO | WO 2005/099761 A1 | 10/2005 |
| WO | WO 2005/110404 A2 | 11/2005 |
| WO | WO 2007/074472 A2 | 7/2007 |
| WO | WO 2008/144019 | 11/2008 |

OTHER PUBLICATIONS http://www.quackwatch.com/01QuackeryRelatedTopics/antiagingpp.html—accessed May 2014.*
Sikora (Experimental Gerontology (2013), vol. 48, pp. 661-666).*
Lamikanra "Development of Anthocyanin Pigments in Muscadine Grapes," *HortScience* 23(3):597-599 (1988).
Mertens-Talcott et al. "Low Concentrations of Quercetin and Ellagic Acid Synergistically influence Proliferation, Cytotoxicity and Apoptosis in MOLT-4 Human Leukemia Cells [1-3]," *J. Nutrition* 133:2669:2674 (2003).
Mertens-Talcott et al. "Ellagic acid and quercetin interact synergistically with resveratrol in the induction of apoptosis and cause transient cell cycle arrest in human leukemia cells," *Cancer Letters* 218:141-151 (2005).

(Continued)

*Primary Examiner* — Susan Hoffman
(74) *Attorney, Agent, or Firm* — Klarquist Sparkman, LLP

(57) ABSTRACT

Disclosed herein is a method of producing a muscadine pomace extract. The method can include combining a bronze muscadine pomace extract with a purple muscadine pomace extract to produce a muscadine pomace extract, wherein the ratio of bronze muscadine pomace extract to purple muscadine pomace extract ranges from 0.1 to 10 (weight to weight), such as from 0.3 to 3 (weight to weight), and the muscadine pomace extract has a polyphenol content of at least 2%. Also disclosed herein is a muscadine pomace extract for use as an antioxidant, such as for use as an anti-aging supplement. The composition can include a muscadine (*Vitis rotundifolia*) pomace extract having a polyphenol content of at least 2% and other active ingredients.

34 Claims, No Drawings

(56) References Cited

OTHER PUBLICATIONS

J. Ponce "Chemical and Economic Analysis of Value-added Product from Muscadine Grape Pomace," *University of Florida* http://ufdc.ufl.edu/UFE0021495/00001 (2007) *Not catalogued until Apr. 2, 2010.

Hudson et al. "Inhibition of Prostate Cancer Growth by Muscadine Grape Skin Extract and Resveratrol through Distinct Mechanisms," *Cancer Research* 67(17):8396-8405 (2007).

Sapcanin et al. "Antioxidant Capacity in the Lipophilic Fraction of Alzheimer's Brain Tissues," *Bosnian J. Basic Medical Sciences* 7(4):317-321 (2007).

Perron and Brumaghim "A Review of the Antioxidant Mechanisms of Polyphenol Compounds Related to Iron Binding," *Cell Biochem Biophys* 53:75-100 (2009).

Cardona et al. "Color and Polyphenolic Stability in Extracts Produced from Muscadine Grape (*Vitis rotundifolia*) Pomace," *J. of Agriculture and Food Chemistry* vol. 57:8421-8425 (2009).

T. Vashisth "Evaluation of Drying Technologies for Muscadine Pomace to Produce an Antioxidant Rich Functional Food Ingredient," *The University of Georgia* http://hdl.handle.net/10724/11195 (2009).

Sandhu and Gu Antioxidant Capacity, Phenolic Content, and Profiling of Phenolic Compounds in the Seeds, Skin, and Pulp of *Vitis rotundifolia* (Muscadine Grapes) As Determined by HPLC-DAD-ESI-MS$^n$", *J. of Agriculture and Food Chemistry* vol. 58:4681-4692 (2010).

Ghanim et al. "A Resveratrol and Polyphenol Preparation Suppresses Oxidative and Inflammatory Stress Response to a High-Fat, High-Carbohydrate Meal," *J. Clin. Endocrinol Metab.* vol. 96(5):1409-1414 (2011).

Soto et al. "Recovery and Concentration of Antioxidants from Winery Wastes," *Molecules* 17:3008-3024 (2012).

Chen et al., "High-speed counter-current chromatography separation and purification of resveratrol and piceid from Polygonum cuspidatum," *Journal of Chromatography A* 907:343-346 (2001).

Dansby "Evaluation of the antioxidant and biological properties of muscadine grape seed extracts," *Dissertation North Carolina State University* 1(45): ii-v (2006).

Ector et al., "Resveratrol concentration in muscadine berries, juice, pomace, purees, seeds and wines," *Am. J. Enol. Vitic.* 47(1):57-62 (1996).

God "Anticancer effects of four varieties of muscadine grape" *Medicinal Food* 10(1):54-59 (2007).

Ke-Lin "Impact of grape seed extract on human health," *China Drinks* 46-47 (2003).

Pastrana-Bonilla et al., "Phenolic content and antioxidant capacity of muscadine grapes," *J. Agricultural and Food Chemistry* 51:497-5503 (2003).

Percival and Sims, "Wine modifies the effects of alcohol on immune cells of mice," *Journal of Nutrition* 130(5):1091-1094 (2000).

Soleas et al., "Comparative evaluation of four methods for assay of cis- and trans-resveratrol," *Am. J. Enol. Vitic.*, vol. 48, No. 2, pp. 169-176 (1997).

Xiao-Jia et al. "Review on health function, processing technology and determination of resveratrol," *Food Research and Development* 27(2):123-126 (2006).

Yilman and Toledo, "Major flavonoids in grape seeds and skins: Antioxidant capacity of catechin, epicatechin, and gallic acid," *J. Agric. Food. Chem.*, 52:255-260 (2004).

Kurilich et al., "Plasma and Urine Responses Are Lower for Acylated vs. Nonacylated Anthocyanins from Raw and Cooked Purple Carrots," *J. Agric. Food Chem.* 53(16): 6537-6542 (2005).

* cited by examiner

METHOD OF PREPARING A MUSCADINE POMACE EXTRACT

CROSS REFERENCE TO RELATED APPLICATION

This is a continuation of U.S. patent application Ser. No. 13/056,559, filed on Jan. 28, 2011, now U.S. Pat. No. 8,512, 771, which is the §371 U.S. National Stage of International Application No. PCT/US2009/052346, filed on Jul. 31, 2009, which was published in English under PCT Article 21(2), which in turn claims the benefit of and priority to U.S. Provisional Application No. 61/085,371 filed on Jul. 31, 2008. The prior applications are incorporated herein by reference in their entirety.

FIELD

This disclosure relates to a muscadine pomace extract and methods of preparing the muscadine pomace extract, such as for use in an anti-aging supplement.

BACKGROUND

Reactive oxygen species (ROS) are obligatory byproducts of aerobic metabolism and thus are generated continuously in humans and other organisms. Humans are also exposed to ROS from exogenous/environmental sources such as pollution, sunlight and diet. While there are different chemical forms of ROS, they all produce deleterious actions on the structure and function of cellular constituents and macromolecules. The intensity of ROS generation/exposure is termed oxidative stress.

Oxidative stress is associated with the pathogenesis of chronic inflammatory diseases such as diabetes, cancer, atherosclerosis and other cardiovascular diseases as well as with degenerative diseases such as Alzheimer's disease and Parkinson's disease. Moreover, multiple lines of evidence support the view that oxidative stress is a central mechanism underlying normal aging. Accordingly, a need exists to develop treatments to inhibit oxidative stress.

SUMMARY

Minimizing oxidative stress is thought to be critical for health and longevity. Epidemiological data show strong benefits conferred by diets rich in antioxidant nutrients. Apart from the classic antioxidant vitamins (vitamins C and E), dietary plants contain a number of polyphenols that appear to lower oxidative stress both acutely and chronically upon consumption. Several in vitro assays have been developed to measure the antioxidant capacity of different foods and there is a strong correlation between polyphenol content and antioxidant capacity.

Although plants including grapes offer a promising source of antioxidants, there are significant obstacles to the widespread use of phytochemicals in human populations. For example, the bioavailability of an active agent in food is often sub-optimal for use as antioxidants. Active agents may also be concentrated in certain parts of a plant that are either underrepresented or discarded in the typical preparation of a foodstuff for consumption. Different species of related foods may also have biochemical differences that render them less optimal for therapeutic use.

The inventors have determined the antioxidant capacity of a muscadine pomace extract and a Japanese knotweed extract separately or in combination (in either a mixture or dietary supplement) as measured by an Oxygen Radical Absorbance Capacity (ORAC) assay. Both hydrophilic antioxidant capacity and lipophilic antioxidant capacity of the samples were measured. These studies demonstrated a strong synergistic effect of the muscadine pomace extract and the Japanese knotweed root extract in a mixture or dietary supplement in producing lipophilic antioxidant capacity. The selective synergy exhibited in the lipophilic conditions was unexpected. These findings demonstrated the improved antioxidant capacity of a mixture and dietary supplement containing both Japanese knotweed extract, at least as a source of substantially pure resveratrol, and a muscadine pomace extract when compared to either of the extracts alone.

Disclosed herein are compositions with improved antioxidant activity. In some disclosed embodiments, the composition includes a muscadine (*Vitis rotundifolia*) pomace extract having a polyphenol content of at least 2% and resveratrol from a source other than muscadine (such as a Japanese knotweed root extract) with a minimum purity of at least 5%, wherein a ratio of muscadine polyphenols to trans-resveratrol is in the range of 0.1/1 to 10/1 (weight to weight), thereby providing a composition with antioxidant activity. In a particular example, the composition includes a muscadine (*Vitis rotundifolia*) pomace extract having a polyphenol content of at least 2% and resveratrol from a source other than muscadine (such as a Japanese knotweed root extract) with a minimum purity of at least 5%, wherein a ratio of muscadine pomace extract to resveratrol is in the range of 0.2/1 to 50/1 (weight to weight), such as 5/1 to 50/1 (weight to weight) or 20/1 to 50/1 (weight to weight), thereby providing a composition with antioxidant activity. In some examples, the composition has a total ORAC of at least 24 µmole Trolox Equivalents per mg polyphenol (µmoleTE/mg polyphenol).

In some examples, the muscadine (*Vitis rotundifolia*) pomace extract has a total polyphenol content of about 4% and the composition has a ratio of muscadine pomace extract to trans-resveratrol of about 18 to 1 (weight to weight). In an example, the composition has a ratio of muscadine polyphenols to resveratrol of about 0.75 to 1 (weight to weight). In certain examples, the muscadine pomace extract can include 20% to 50% solids in a liquid. For example, the muscadine pomace extract comprises about 40% solids in a liquid. In some examples, resveratrol includes at least 98% trans-resveratrol extracted from Japanese Knotweed (*Polygonum cuspidatum*) root. The disclosed compositions, in some examples, can further include an elderberry extract, a purple carrot extract, an excipient (such as glycerin, sorbitol, colloidal silicon dioxide, or a natural flavoring additive) or a combination thereof. In a particular example, the composition includes a muscadine pomace extract at 23% to 32% of the total composition, resveratrol at 1.2% to 3.0% of total, a purple carrot extract at 0.12% to 0.20% of total, an elderberry extract at 0.4% to 0.6% of total, sorbitol at 50% to 61% of total, a 99.7% glycerin composition at 8% to 12% of total, and colloidal silicon dioxide at 1% to 2% of total.

In a more particular example, the composition includes muscadine pomace extract (containing about 4.1% polyphenols) at about 28.9% of total, resveratrol at about 1.65% of total, purple carrot extract at about 0.16% of total, elderberry extract at about 0.48% of total, sorbitol at about 54.8% of total, 99.7% glycerin composition at about 10% of total, colloidal silicon dioxide at about 2% of total, Concord grape extract at about 1.27%, Cabernet grape extract at about 0.16% and red grape powder at about 0.48%.

In another particular example, the composition includes muscadine pomace extract (containing about 5% polyphenols) at about 23.77% of total, resveratrol at about 1.65% of total, purple carrot extract at about 0.16% of total, elderberry extract at about 0.48% of total, sorbitol at about 60% of total, 99.7% glycerin composition at about 10% of total, colloidal silicon dioxide at about 2% of total, Concord grape extract at about 1.27%, Cabernet grape extract at about 0.16% and red grape powder at about 0.48%.

Any of the disclosed compositions can be provided in a non-beverage food, a beverage, or dietary supplement in the form of a liquid or solid. Further, any of the disclosed compositions can be used as an antioxidant agent, such as an anti-aging supplement, including skin improving agents. For example, methods of preventing or inhibiting cellular aging are disclosed, including administering to a subject in need thereof a dose of a disclosed composition sufficient to prevent or inhibit one or more processes associated with cellular aging, such as preventing or inhibiting free radical formation or activity in the subject that ingests the composition.

Methods of producing the disclosed antioxidant compositions are also provided herein. These methods can include combining a muscadine (*Vitis rotundifolia*) pomace extract having a polyphenol content of at least 2% and resveratrol from a source other than muscadine with a minimum purity of at least 5% trans-resveratrol, wherein a ratio of muscadine polyphenols to trans-resveratrol is in the range of 0.1/1 to 10/1 (weight to weight), thereby producing a muscadine pomace extract and trans-resveratrol mixture with antioxidant activity. In some examples, the methods can include combining a muscadine (*Vitis rotundifolia*) pomace extract having a polyphenol content of at least 2% and resveratrol from a source other than muscadine (such as a Japanese knotweed root extract) with a minimum purity of at least 5% trans-resveratrol, wherein a ratio of muscadine pomace extract to resveratrol is in the range of 0.2/1 to 50/1 (weight to weight), such as 5/1 to 50/1 (weight to weight) or 20/1 to 50/1 (weight to weight), including 18 to 1 (weight to weight), thereby providing a composition with antioxidant activity.

The disclosed methods can further include preparing the muscadine pomace extract prior to combining the muscadine pomace extract with trans-resveratrol. In one particular example, preparing the muscadine pomace extract includes combining bronze muscadine pomace extract with purple muscadine pomace extract. In other examples, preparing the muscadine pomace extract includes preparing an extract from a mixture of bronze muscadine pomace and purple muscadine pomace.

In a particular example, the method includes preparing the muscadine pomace extract by combining bronze muscadine pomace extract and purple muscadine pomace extract in which the ratio of bronze muscadine pomace extract to purple muscadine pomace extract ranges from 0.1 to 10 (weight to weight), such as from 0.3 to 3 (weight to weight). In a more particular example, the ratio of bronze muscadine pomace extract to purple muscadine pomace extract is about 2.25 to 1 (weight to weight).

The foregoing and other features of the disclosure will become more apparent from the following detailed description.

DETAILED DESCRIPTION

I. Abbreviations and Terms:
(a) Abbreviations
FRAP: Ferric Reducing Ability of Plasma
mg: milligram
ml: milliliter
ORAC: Oxygen Radical Absorbance Capacity
ROS: Reactive oxygen species
TE: Trolox Equivalent
TEAC: Trolox Equivalent Antioxidant Capacity
wt: weight
(b) Terms The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. It is further to be understood that any quantitative values are approximate whether the word "about" or "approximately" or the like are stated or not. All percentages and ratios are calculated by weight unless otherwise indicated.

Administration: To provide or give a subject an agent, such as a composition that includes a muscadine pomace extract and trans-resveratrol by any effective route. Exemplary routes of administration include, but are not limited to, oral, injection (such as subcutaneous, intramuscular, intradermal, intraperitoneal, intravenous, and intratumoral), sublingual, transdermal, intranasal, topical and inhalation routes.

Antioxidant activity: Activity including scavenging and neutralizing oxidative free radicals. Antioxidant activity can be measured using the methods disclosed herein as well as those known in the art, including the Oxygen Radical Absorbance Capacity (ORAC) assay, the Ferric Reducing Ability of Plasma (FRAP) assay, and the Trolox Equivalent Antioxidant Capacity (TEAC) assay. In an example, a composition has antioxidant activity and can be used as an antioxidant if it has a total ORAC of at least 24 µmole Trolox Equivalents per mg polyphenol (µmoleTE/mg polyphenol).

Elderberry (*Sambucus nigra*): A plant belonging to the Adoxaceae family found in Europe and North America with several regional varieties or subspecies. The flowers are in flat corymbs. The berries are black to glaucous blue and contain anthocyanins and other polyphenolics in which the amount and type of anthocyanins and other polyphenolics vary depending upon the variety.

An "elderberry extract" can be a material obtained by extracting an elderberry according to any extraction method known to one of skill in the art, so long as it has the desired activity (e.g., color stabilizing activity, antioxidant activity or a combination thereof). For example, the elderberry extract can include, a fruit juice obtained by compressing elderberry fruit, or an extract obtained by extracting whole fruit of elderberry or a suitable portion of skin or seed of the fruit according to the conventionally known optional extracting method for those skilled in the art, and the like. Also, a crushed product of an elderberry fruit, or a dried elderberry fruit concentrate can be used as "an elderberry extract."

Excipient: An inactive substance used as a carrier for the active ingredients of a composition. Excipients can include substances that are used to bulk up formulations with very potent active ingredients, allow for convenient and accurate dosage, stabilize the active ingredients, and make the delivery system optically and/or organoleptically acceptable. Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In a particular example, the disclosed anti-aging supplement includes the following excipients: glycerin, sorbitol, colloidal silicon dioxide, and a natural flavoring additive.

Inhibiting (including preventing) cellular aging: Inhibiting (for example preventing) one or more processes associated with cellular aging, such as inhibiting free radical formation or activity in the subject that ingests the composition. Preventing cellular aging refers to an intervention that ameliorates a sign or symptom of cellular aging. Preventing includes prophylaxis to delay the onset of one or more processes associated with cellular aging. Prevention or inhibition of cellular aging does not require a total absence of cellular aging. In a particular example, a disclosed composition decreases or delays a process associated with cellular aging by at least 10%, at least 20%, at least 50%, or even at least 90%. Such decreases can be measured using the methods disclosed herein as well as those known in the art.

Muscadine Grape (*Vitus rotundifolia*): Grapes native to the southeastern United States, and found in the wild from Delaware to the Gulf of Mexico and westward to Missouri, Kansas, Oklahoma, and Texas. Muscadines are well adapted to the warm, humid conditions of the southeastern United States. The fruit is borne in small, loose clusters of 3-40 grapes, quite unlike the large, tight bunches characteristic of European and American grapes. The round, 1 to 1½ inch fruits have a thick, tough skin and contain up to 5 hard, oblong seeds. In color the fruits range from greenish bronze through bronze, pinkish red, purple and almost black.

Many different varieties of muscadine grapes are available, including female (pistillate) varieties such as Black Beauty, Black Fry, Darlene, Fry, Higgins, Jumbo, Scuppernong, Sugargate, Summit, Supreme, and Sweet Jenny, and self-fertile varieties such as Carlos, Cowart, Dixieland, Dixie Red, Fry Seedless, Magnolia, Nesbitt, Noble, Redgate, Regale and Sterling.

For example the bronze colored varieties of muscadine grapes are identified by those skilled in the art as including Carlos, Chowan, Doreen, Higgins, Magnolia, Nevermiss, Pamlico, Roanoke, Scuppernong, Sterling, and Summit cultivars. Purple to black colored varieties include Albermarle, Bountiful, Cowart, GA-1, Hunt, NC-1, Noble, Regale, Tarheel, and Jumbo.

The phytochemical constituents of the whole muscadine grape differ from *Vitis vinifera*. Muscadines have a higher total phenolic content distinguished by high ellagic, gallic, and flavonoid glycoside concentrations. The presence of ellagic acid in muscadine grapes is unique and is found in the form of free ellagic acid, ellagic acid glycosides, methoxylated derivatives and ellagitannins. Another unique feature is the anthocyanin chemistries observed in muscadines. Present as 3,5-diglucosides (as opposed to 3-glucosides) of delphinidin, cyanidin, petunidin, peonidin, and malvidin in non-acylated forms, these compounds and the natural color influence from other other anthocyanins present within the grape impart a dark purple color to juice and pomace. Purple pomace extracts contain anthocyanins while bronze pomace extracts do not.

The red and purple colored anthocyanins are polyphenolic compounds that have antioxidant properties. Flavonols are the second most abundant flavonoids present in whole muscadines. The major phenolics reported for the muscadine skin fraction (in descending order) are ellagic acid, myricetin, quercetin, and kaempferol while those reported for seeds are epicatechin, catechin and gallic acid (Patrana-Bonilla et al. *J. Agric. Food Chem.* 51:5497-5503, 2003).

Pharmaceutically Acceptable Vehicles: The pharmaceutically acceptable vehicles (carriers) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more compositions, such as one or more muscadine compositions, and additional pharmaceutical agents.

In general, the nature of the vehicle will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid vehicles can include, for example, pharmaceutical grades of mannitol, lactose, starch, or magnesium stearate. In addition to biologically-neutral vehicles, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: The term purified does not require absolute purity; rather, it is intended as a relative term. Thus, for example, a purified substance is one in which the substance is more enriched than the substance in its natural environment, for example in a fruit (e.g., grape). In one embodiment, a preparation is purified such that the substance represents at least about 5% (such as, but not limited to, at least 10%, 20%, 30%, 40%, 50%, 70%, 80%, 90%, 95%, 98% or 99%) of the total content of the preparation. In an example, a disclosed composition with antioxidant activity includes trans-resveratrol with a minimum of purity of at least 50%, 70%, 80%, 90%, 95%, 98% or 99% of the total resveratrol preparation (by weight).

Pomace: The skins, seeds, and pulp remaining following juice extraction. In one example, a pomace extract is a bronze muscadine pomace extract, a purple muscadine pomace extract or a combination thereof. Many different varieties of muscadine grape pomaces are available as starting materials, and they include female (pistillate) varieties such as Black Beauty, Black Fry, Darlene, Fry, Higgins, Jumbo, Scuppernong, Sugargate, Summit, Supreme, and Sweet Jenny, and self-fertile varieties such as Carlos, Cowart, Dixieland, Dixie Red, Fry Seedless, Magnolia, Nesbitt, Noble, Redgate, Regale and Sterling.

Muscadine pomace contains phenolic compounds, including gallic acid and ellagic acid, having antioxidant properties.

Purple carrot (*Daucus carota*): a cultivar of carrot containing anthocyanin pigments. A "purple carrot extract" can be material obtained by extracting a purple carrot according to any extraction method known to one of skill in the art, so long as it has the desired activity (e.g., color stabilizing activity, antioxidant activity or a combination thereof). In an example, a purple carrot extract has the property of stabilizing muscadine color pigment and can therefore be subsequently utilized as color-stabilizing additive.

Resveratrol: A phytoalexin that is a stilbenoid, a derivate of stilbene, and is produced in plants with the help of the enzyme stilbene synthase. Resveratrol exists as two structural isomers: cis- and trans- resveratrol. Trans-resveratrol can undergo isomerisation to the cis- form when heated or exposed to ultraviolet irradiation.

Resveratrol is found in widely varying amounts in grapes, raspberries, mulberries, in plums, peanuts, berries of Vaccinium species, including blueberries, bilberries, and cranberries, some pines, such as Scots pine and eastern white pine, and the roots and stalks of giant knotweed and Japanese knotweed. In grapes, resveratrol is found primarily in the skin and seeds. The amount of resveratrol found in grape skins varies with the grape cultivar, its geographic origin, and exposure to fungal infection.

As used herein, the term resveratrol can include natural trans-resveratrol extracted from a plant, such as grapes, or synthetic trans-resveratrol. As used herein, the term resveratrol can include modified formulations of trans-resveratrol such as microencapsulated or water dispersible forms.

Subject: Living multi-cellular vertebrate organisms, a category that includes both human and veterinary subjects.

Therapeutically Effective Amount: An amount of a composition that alone, or together with an additional agent(s) (for example additional antioxidants), induces the desired response (e.g., prevents or inhibits cellular aging). The preparations disclosed herein can be administered in therapeutically effective amounts.

In one example, a desired response is to inhibit or decrease free radical production or activities associated with one or more cellular aging processes in a subject to whom the composition is administered. Free radical production or activity does not need to be completely eliminated for the composition to be effective. For example, a composition can decrease production or activity by a desired amount, for example by at least 10%, at least 20%, at least 50%, at least 60%, at least 70%, at least 80%, at least 90%, at least 95%, or at least 98%, as compared to free radical production or activity in the absence of the composition.

A therapeutically effective amount of a disclosed muscadine pomace extract composition, can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 to about 500 milligrams of either trans-resveratrol, muscadine polyphenols or a combination thereof daily if administered orally.

Unit dose: A physically discrete unit containing a predetermined quantity of an active material calculated to individually or collectively produce a desired effect, such as a therapeutic effect. A single unit dose or a plurality of unit doses can be used to provide the desired effect or activity, such as antioxidant activity. In one example, a unit dose includes a desired amount of an agent that prevents or inhibits one or more of the processes associated with cellular aging.

II. Description of Several Embodiments

Plant agents have been studied extensively as a potential source of nutriceutical agents that can be used to reduce oxidative stress. Red grapes are among the many foods that have been the subject of intense research. The antioxidant effects of red grapes have been widely attributed to the polyphenolic compounds, such as resveratrol and procyanidins, the latter which appear in substantial quantities in the grapes.

The inventors performed a series of studies to develop a muscadine pomace extract sufficient to promote the maximum solubility of ellagic acid. It has now been discovered that an unconcentrated 65% to 35% bronze muscadine pomace extract to purple muscadine pomace extract (volume to volume) ratio promotes the maximum solubility of ellagic acid between the two pomace extracts.

Determination of the maximum solubility of ellagic acid (which is unique to muscadine grapes) in a muscadine pomace extract allowed extracts to be prepared with enhanced ellagic acid solubility (and thus capture the polyphenol profile of the pomace) which in turn allowed extracts with improved antioxidant activity to be prepared. Thus, disclosed herein are muscadine pomace extracts with improved ellagic acid solubility and methods of using such extracts. For example, the disclosed muscadine extracts can be administered either alone or in combination with other compounds in a non-beverage food, a beverage, dietary supplement or a topical ointment. Also enabled are methods of producing muscadine pomace extracts, including combining a bronze muscadine pomace extract with a purple muscadine pomace extract to produce a muscadine pomace extract, wherein the ratio of bronze muscadine pomace extract to purple muscadine pomace extract ranges from 0.3 to 3 (weight to weight).

Additionally, the inventors determined the antioxidant capacity of the disclosed muscadine pomace extract and a Japanese knotweed extract, standardized to 98% trans-resveratrol, separately or in combination (in either a mixture or dietary supplement) as measured by an ORAC assay. Both hydrophilic antioxidant capacity and lipohilic antioxidant capacity of the samples were measured. These studies demonstrated a strong synergistic effect of the muscadine pomace extract and Japanese knotweed root extract, standardized to 98% trans-resveratrol, in a mixture or dietary supplement in producing lipophilic antioxidant capacity. The selective synergy exhibited in the lipophilic conditions was unexpected. Also, while the muscadine extract utilized in the composition can be a natural extract which can vary by species, extraction process, etc. as long as the disclosed ratio of muscadine polyphenols to resveratrol is maintained, the synergistic lipophilic antioxidant activity was preserved.

These findings demonstrate the improved lipophilic antioxidant capacity of a mixture and dietary supplement containing both Japanese knotweed extract, standardized to 98% trans-resveratrol, and a muscadine pomace extract when compared to either of the extracts alone. Importantly, oxidative processes occurring in lipophilic environments are thought to underlie and/or initiate the pathogenesis of multiple disease states such as low density lipoprotein (LDL) oxidation in atherosclerosis and obesity-induced insulin resistance in Type II diabetes. Moreover, oxidation of dietary lipids within the gastrointestinal tract leads to absorption of cytotoxic and genotoxic lipid peroxidation products such as malondialdehyde (MDA). Thus, the disclosed compositions possessing high lipophilic antioxidant capacity may confer beneficial actions in counteracting the deleterious consequences of lipid oxidation mentioned above.

This discovery has enabled muscadine pomace extract compositions with improved antioxidant activity and methods of producing such compositions. For example, muscadine pomace extract compositions with antioxidant activity are disclosed herein that can be administered in a non-beverage food, a beverage, a liquid or solid dietary supplement or a topical ointment. Methods of producing the disclosed compositions can include combining a muscadine (*Vitis rotundifolia*) pomace extract having a polyphenol content of at least 2% and trans-resveratrol from a source other than muscadine with a minimum purity of at least 5%, wherein a ratio of muscadine polyphenols to trans-resveratrol is in the range of 0.1/1 to 10/1 (weight to weight), thereby producing a muscadine pomace extract and trans-resveratrol mixture with antioxidant activity. Methods of producing the disclosed compositions can also include combining a muscadine (*Vitis rotundifolia*) pomace extract having a polyphenol content of at least 2% and trans-resveratrol from a source other than muscadine with a minimum purity of at least 5%, wherein a ratio of muscadine pomace extract to trans-resveratrol is in the range of 0.2/1 to 50/1 (weight to weight), such as 5/1 to 50/1 (weight to weight) including 20/1 to 50/1 (weight to weight), such as 18 to 1 (weight to weight), thereby producing a muscadine pomace extract and trans-resveratrol mixture with antioxidant activity.

Lipophilic antioxidants have been found to be effective at preventing various types of skin damage, such as by, but not limited to, inhibiting lipid peroxidation and the products produced by lipid peroixdation, such as cross-linking agents. It is known that oxidative stress is a central mechanism underlying normal aging. It is shown herein that the disclosed compositions have improved lipophilic antioxidant activity. Based on these observations, methods of inhibiting cellular aging, such as preventing or inhibiting free radical production or activity, are disclosed. The methods include using the disclosed compositions (e.g., dietary supplements) with improved antioxidant capacity as an anti-aging supplement. For example, methods of preventing or reducing one or more processes associated with cellular aging, such as reducing or inhibiting free radical production or activity in a subject that ingests the mixture or dietary supplement composition, are enabled.

A. Muscadine pomace extracts

Disclosed herein are muscadine pomace extracts derived from bronze muscadine pomace and purple muscadine pomace. In some embodiments, the ratio of bronze muscadine pomace extract to purple muscadine pomace extract in the muscadine pomace extract ranges from 0.3 to 3 (weight to weight). For example, the ratio of bronze muscadine pomace extract to purple muscadine pomace extract is about 2.75 to about 1 (weight to weight), 2.5 to about 1 (weight to weight), about 2.25 to about 1 (weight to weight), about 2 to about 1 (weight to weight), about 1.5 to about 1 (weight to weight), or about 1 to about 1 (weight to weight). As used herein the term "about" is defined as ±0.5. In a particular example, the ratio of bronze muscadine pomace extract to purple muscadine pomace extract is about 2.25 to about 1 (weight to weight).

In certain embodiments, the disclosed muscadine (*Vitis rotundifolia*) pomace extract has a polyphenol content of at least 2%. For example, the polyphenol content is at least 3%, at least 3.5%, at least 4%, at least 4.5%, at least 5%, at least 6%, at least 8%, at least 10%, at least 12%, or at least 14%. In a particular example, the muscadine (*Vitis rotundifolia*) pomace extract has a polyphenol content of about 4%.

In some embodiments, the disclosed muscadine pomace extracts include 20% to 50% solids, such as at least 25%, at least 30%, at least 35%, at least 37%, at least 40%, at least 42%, at least 44%, at least 46% or at least 48%, in a liquid. In a particular example, the extract includes about 40% solids in a liquid.

B. Methods of making muscadine pomace extracts

Methods of making muscadine pomace extracts are also disclosed, in which the ratio of bronze muscadine pomace extract to purple muscadine pomace extract ranges from 0.3 to 3 (weight to weight). In one disclosed embodiment, muscadine pomace extracts are prepared by combining a bronze muscadine pomace extract with a purple muscadine pomace extract. In one particular example, a muscadine pomace extract is prepared by combining bronze muscadine pomace extract with purple muscadine pomace extract in which the ratio of bronze muscadine pomace extract to purple muscadine pomace extract ranges from 0.1 to 10 (weight to weight), including from 0.3 to 3 (weight to weight), such as about 2.75 to about 1 (weight to weight), 2.5 to about 1 (weight to weight), about 2.25 to about 1 (weight to weight), about 2 to about 1 (weight to weight), about 1.5 to about 1 (weight to weight), or about 1 to about 1 (weight to weight). In an even more particular example, a muscadine pomace extract is prepared by combining bronze muscadine pomace extract with purple muscadine pomace extract in which the ratio of bronze muscadine extract to purple muscadine pomace extract is about 2.25 to 1 (weight to weight).

In some examples, methods of making muscadine pomace extracts can include preparing bronze muscadine pomace extracts and purple muscadine pomace extracts separately. For example, bronze muscadine pomace and purple muscadine pomace are separately extracted with water, preferably heated. Preparing bronze muscadine pomace extract and purple muscadine pomace extract can further include fermenting the bronze muscadine pomace extract and purple muscadine pomace extract to remove extracted sugars. In one example, fermentation is performed following extracting the bronze muscadine pomace and purple muscadine pomace but prior to combining the bronze muscadine pomace extract with the purple muscadine pomace extract to produce a disclosed muscadine pomace extract. In other examples, fermentation is performed after combining the bronze muscadine pomace extract with purple muscadine pomace extract in the desired post extraction ratio (such as at about a 2:25 to 1 bronze to purple ratio).

Fermentation may be performed by any method known to one of skill in art, including those described herein. For example, fermentation can include adding yeast and yeast nutrients to the pomace and letting the extract ferment until the residual sugar content is converted to ethanol. Typically one uses 2 pounds of yeast per 1000 gallons of 1× (unconcentrated) extract. In such an example, fermentation is typically complete after three days. In other examples, the amount and/or strain of yeast and duration and temperature of fermentation may vary according to individual methods known to one of skill in art. In some examples, enzymes can be used to clarify and/or settle residues or to improve extraction yield in the pomace extracts. For example, these enzymes can include pectinase or a blend of enzymes from *Aspergillus niger* and are commercially available from sources such as Scott Laboratories. These enzymes may be added to the pomace extract before or during fermentation.

In some embodiments, preparing bronze muscadine pomace extracts and purple muscadine pomace extracts includes filtering the bronze muscadine pomace extract and purple muscadine pomace extract. For example, bronze muscadine pomace extracts and purple muscadine pomace extracts can be filtered prior to and/or following fermentation. Filtration can be performed according to general methods known to those of skill in the art, including filtration methods disclosed herein. In a particular example, extracts are filtered through sieves of appropriate mesh size, such as USP mesh (typically 120 mesh) or a similar cloth filter (such as filters commercially available from Millipore Corporation).

In other embodiments, preparing a muscadine pomace extract can include combining bronze muscadine pomace and purple muscadine pomace at a desired ratio and extracting bronze muscadine pomace and purple muscadine pomace simultaneously. For example, the bronze muscadine pomace and purple muscadine pomace are simultaneously extracted with water, preferably heated, to produce the disclosed muscadine pomace extract. In some embodiments, this method can further include fermenting the muscadine pomace extract to remove extracted sugars. As previously described, any fermentation method known to one of skill in art, including those described herein, can be used. For example, fermentation can include adding yeast and yeast nutrients to the pomace and letting the extract ferment until the residual sugar content is converted to ethanol. In one example, fermentation includes adding 2 pounds of yeast per 1000 gallons of 1× extract and allowing the extract to remain at room temperature for approximately 3 days or until the residual sugar content is converted to ethanol. This disclosed method can also include filtering the muscadine pomace extract. For example, the muscadine pomace extract can be filtered before and/or following fermentation. Filtration can be performed according to general methods known to those of skill in the art, including filtration methods disclosed herein.

In certain embodiments, methods of making muscadine pomace extracts further include concentrating the bronze muscadine pomace extract and the purple muscadine pomace extract so that each extract includes 20% to 50% solids, such as at least 25%, at least 30%, at least 35%, at least 37%, at least 40%, at least 42%, at least 44%, at least 46% or at least 48%, in a liquid. In a particular example, the extracts are concentrated so that each extract includes about 40% solids in a liquid. Generally known methods for concentrating samples, including methods for concentrating samples disclosed herein can be used to concentrate the bronze and purple extracts.

In a particular example, to prepare a muscadine pomace extract at 40% solids, the muscadine pomace extract is dried down into a powder form and re-constituted in water at 40% solids level. Alternatively, and a more acceptable commercial approach, is to concentrate by removal of the extraction solvent through evaporation under vacuum. This can be achieved through a batch or continuous process. Batch processes involve placing the extract in a vessel, pulling a vacuum of 20-29" of mercury while heating the vessel jacket to provide energy to increase the vapor pressure of the solvent. Solvent vapors are condensed external to the vessel and the rate of condensation controls the temperature of the condensate. The same principles apply to a continuous evaporation process but the advantage being the shortened period of time that the condensate is exposed to elevated temperatures. Both processes are applicable to the concentration of a muscadine pomace extract described herein.

In particular embodiments, methods of making muscadine pomace extracts include extracting bronze and purple pomace separately followed by filtering each of the extracts prior to combining the bronze and purple pomace extract at the desired ratio. In some examples, this method can further include fermenting the combined muscadine pomace extract to remove extracted sugars. As previously described, any fermentation method known to one of skill in art, including those described herein, can be used. In one example, the method includes more than one filtering step, such as filtering the extract prior to and following fermentation. In some examples, the method can further include concentrating the extract, as described herein. For example, the method can include concentrating the extract by removal of the extraction solvent through evaporation under vacuum.

C. Compositions with antioxidant activity

Disclosed herein are compositions with improved antioxidant activity. In some disclosed embodiments, the compositions includes a muscadine (*Vitis rotundifolia*) pomace extract having a polyphenol content of at least 2% and trans-resveratrol from a source other than muscadine grapes (such as a Japanese knotweed root extract) with a minimum purity of at least 5%, wherein a ratio of muscadine polyphenols to trans-resveratrol is in the range of 0.1/1 to 10/1 (weight to weight), thereby providing a composition with antioxidant activity.

In some examples, the composition includes a muscadine (*Vitis rotundifolia*) pomace extract having a total polyphenol content of at least 3%, at least 3.5%, at least 4%, at least 4.5%, at least 5%, at least 6%, at least 8%, at least 10%, at least 12% or at least 14% and trans-resveratrol from a source other than muscadine grapes with a minimum purity of at least 5%, at least 10%, at least 25%, at least 50%, at least 60%, at least 70%, at least 75%, at least 80%, at least 85%, at least 90%, at least 95%, at least 97%, or at least 98%. In a particular example, the composition includes a muscadine (*Vitis rotundifolia*) pomace extract with a polyphenol content of about 4% and trans-resveratrol from a source other than muscadine grapes with a minimum purity of at least 98%.

In particular embodiments, the composition includes a muscadine pomace extract with 20% to 50% solids, such as at least 23%, at least 25%, at least 30%, at least 35%, at least 37%, at least 40%, at least 42%, at least 44%, at least 46% or at least 48%, in a liquid. In a particular example, the extract includes about 40% solids in a liquid.

In some embodiments, the resveratrol includes at least 5% trans-resveratrol, such as at least 10% trans-resveratrol, at least 20% trans-resveratrol, at least 30% trans-resveratrol, at least 40% trans-resveratrol, at least 50% trans-resveratrol, at least 55%, at least 60%, at least 70%, at least 75%, at least 80%, at least 85%, at least 90%, at least 95%, at least 97%, or at least 98% trans-resveratrol. In particular embodiments, resveratrol includes at least 50% trans-resveratrol, such as at least 55%, at least 60%, at least 70%, at least 75%, at least 80%, at least 85%, at least 90%, at least 95%, at least 97%, or at least 98% trans-resveratrol extracted from Japanese Knotweed (*Polygonum cuspidatum*) root. It is contemplated that other trans-resveratrol sources can be used in the disclosed composition including synthetic trans-resveratrol.

In certain embodiments, the disclosed antioxidant composition has a ratio of muscadine polyphenols to trans-resveratrol of at least 0.1 to 1 (weight to weight), such as, 0.25 to 1, 0.5 to 1, 0.6 to 1, 0.65 to 1, 0.7 to 1, 0.75 to 1, 0.8 to 1, 0.9 to 1 or 1 to 1 (weight to weight). In other embodiments, the ratio of muscadine polyphenols to trans-resveratrol may be as high as 10 to 1 (weight to weight), such as 2 to 1, 3 to 1, 4 to 1, 5 to 1, 7.5 to 1 or 9 to 1 (weight to weight). In a particular example the disclosed antioxidant composition has a ratio of muscadine polyphenols to trans-resveratrol of 0.75 to 1 (weight to weight).

In certain embodiments, the disclosed antioxidant composition has a ratio of muscadine pomace extract to trans-resveratrol ranging from 0.2/1 to 50/1 (weight to weight), such as 0.5 to 1, 1 to 1, 5 to 1, 10 to 1, 15 to 1, 20 to 1, 22 to 1, 25 to 1, 30 to 1, 35 to 1, 40 to 1, or 45 to 1 (weight to weight).

In some embodiments, the disclosed compositions with antioxidant activity have a total ORAC of at least 21 µmole Trolox Equivalents per mg polyphenol (µmoleTE/mg polyphenol), such as at least 22 µmoleTE/mg polyphenol), at least 24 µmoleTE/mg polyphenol), at least 26 µmole µmoleTE/mg polyphenol, at least 28 µmoleTE/mg polyphenol, or at least 30 µmoleTE/mg polyphenol. In one example, a disclosed composition has a total ORAC of 24 µmoleTE/mg polyphenol.

The disclosed compositions, in some examples, can further include an elderberry extract, a purple carrot extract, an excipient (such as glycerin, sorbitol, colloidal silicon dioxide, or a natural flavoring additive) or a combination thereof. For example, the elderberry extract and purple carrot extract can be included to provide color to the composition or for additional antioxidant activity.

In a particular example, the composition includes a muscadine pomace extract (containing about 4% to 5% polyphenol content) at 23% to 32% of the total composition (such as at 23%, 24%, 25%, 26%, 27%, 28%, 29%, 30%, 31% or 32%), trans-resveratrol at 1.2% to 3.0% of total (such as at 1.3%, 1.5%, 1.7%, 1.9%, 2.1%, 2.3%, 2.5%, 2.7% or 2.9%), a purple carrot extract at 0.12% to 0.20% of total (such as at 0.12%, 0.14%, 0.16%, 0.18%, or 0.20%), an elderberry extract at 0.4% to 0.6% of total (such as at 0.4%, 0.45%, 0.5%, 0.55%, or 0.6%), sorbitol at 50% to 61% (such as at 51%, 52%, 53%, 54%, 55%, 56%, 57%, 58%, 59%, or 60%) of total, a 99.7% glycerin composition at 8% to 12% of total (such as at 8%, 9%, 10%, 11% or 12%), and colloidal silicon dioxide at 1% to 2% (such as at 1.2%, 1.5%, 1.7%, or 2%) of total. In other particular examples, the composition includes a muscadine pomace extract (containing from 2% to 14% muscadine polyphenols on a liquid weight basis) at 8% to 60% of the total composition and trans-resveratrol at 1.2% to 3.0% of the total composition.

In a more particular example, the composition includes muscadine pomace extract at 28% to 30% of total, resveratrol at 1% to 2% of total, the purple carrot extract at 0.1% to 0.2% of total, an elderberry extract at 0.4% to 0.5% of total, sorbitol at 53% to 56% of total, a 99.7% glycerin composition at 9% to 11% of total, colloidal silicon dioxide at 1.5% to 2% of total, Concord grape extract at about 1% to 2%, Cabernet grape extract at 0.1% to 0.2% and red grape powder at 0.4% to 0.5%.

In an even more particular example, the composition includes muscadine pomace extract (containing 4.1% polyphenol content) at about 28.9% of total, trans-resveratrol at about 1.65% of total, purple carrot extract at about 0.16% of total, elderberry extract at about 0.48% of total, sorbitol at about 54.8% of total, 99.7% glycerin composition at about 10% of total, colloidal silicon dioxide at about 2% of total, Concord grape extract at about 1.27%, Cabernet grape extract at about 0.16% and red grape powder at about 0.48%.

In another particular example, the composition includes muscadine pomace extract at 23% to 25% of total, resveratrol at 1% to 2% of total, the purple carrot extract at 0.1% to 0.2% of total, an elderberry extract at 0.4% to 0.5% of total, sorbitol at 58% to 61% of total, a 99.7% glycerin composition at 9% to 11% of total, colloidal silicon dioxide at 1.5% to 2% of total, Concord grape extract at about 1% to 2%, Cabernet grape extract at 0.1% to 0.2% and red grape powder at 0.4% to 0.5%.

In another even more particular example, the composition includes muscadine pomace liquid extract (containing 5% polyphenol content) at about 23.77% of total, trans-resveratrol at about 1.65% of total, purple carrot extract at about 0.16% of total, elderberry extract at about 0.48% of total, sorbitol at about 60.05% of total, 99.7% glycerin composition at about 10% of total, colloidal silicon dioxide at about 2% of total, Concord grape extract at about 1.27%, Cabernet grape extract at about 0.16% and red grape powder at about 0.48%.

Any of the disclosed compositions can be provided in a non-beverage food, a beverage, or a liquid or solid dietary supplement. In some examples, the disclosed compositions are provided as a beverage. The compositions herein (particularly the food, beverage and dietary supplement compositions) can be fortified with one or more nutrients, especially one or more vitamins and/or minerals. The U.S. Recommended Daily Intake (USRDI) for vitamins and minerals are defined and set forth in the Recommended Daily Dietary Allowance-Food and Nutrition Board, National Academy of Sciences-National Research Council. Unless otherwise specified herein, wherein a given mineral is present in the product, the product comprises at least about 1%, such as at least about 5%, at least about 10%, at least about 20%, at least about 50%, at least about 75%, at least about 100%, at least about 150% of the USRDI of such mineral. Unless otherwise specified herein, wherein a given vitamin is present in the product, the product comprises at least about 1%, such as at least about 5%, at least about 10%, at least about 20%, at least about 50%, at least about 75%, at least about 100%, at least about 150% of the USRDI of such vitamin. The quantity of vitamins and minerals to be added can be dependent on processing and the concentration of the other ingredients within the formulation.

Non-limiting examples of such vitamins and minerals include iron, zinc, copper, calcium, phosphorous, niacin, thiamin, folic acid, pantothenic acid, iodine, vitamin A, vitamin C, vitamin B2, vitamin B3, vitamin B6, vitamin B12, vitamin D, vitamin E, and vitamin K. Commercially available sources of the vitamins and minerals may also be included in the present compositions.

For example, any soluble salt of these minerals suitable for inclusion in edible products can be used, for example, magnesium citrate, magnesium gluconate, magnesium sulfate, zinc chloride, zinc sulfate, potassium iodide, copper sulfate, copper gluconate, and copper citrate. Sources of calcium can include, for example, amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium titrate, calcium gluconate, calcium realate, calcium tantrate, and calcium lactate, and in particular calcium citrate-malate. As used herein, "vitamin A" includes, but is not limited to, retinol, β-carotene, retinol palmitate, and retinol acetate. The vitamin A can be in the form of, for example, an oil, beadlets or encapsulated. Encapsulated ascorbic acid and edible salts of ascorbic acid can also be utilized. Sources of iodine include iodine-containing salts, such sodium iodide, potassium iodide, potassium iodate, sodium iodate, or mixtures thereof. These salts may be encapsulated. Acceptable forms of iron are well-known in the art. The amount of iron compound incorporated into the composition will vary widely depending upon the level of supplementation desired in the final product and the targeted consumer. Iron fortified compositions of the present disclosure typically contain from about 5% to about 100%, such as about 15%, about 25%, about 40%, about 50%, about 70%, about 80%, or about 90% of the USRDI for iron.

Ferrous iron is typically better utilized by the body than ferric iron. Highly bioavailable ferrous salts that can be used in the disclosed ingestible compositions are ferrous sulfate, ferrous fumarate, ferrous succinate, ferrous gluconate, ferrous lactate, ferrous tartarate, ferrous citrate, ferrous amino acid chelates, as well as mixtures of these ferrous salts. While ferrous iron is typically more bioavailable, certain ferric salts can also provide highly bioavailable sources of iron. Highly bioavailable ferric salts that can be used in the food or beverage compositions of the present disclosure are ferric saccharate, ferric ammonium citrate, ferric citrate, ferric sulfate, as well as mixtures of these ferric salts. Combinations or mixtures of highly bioavailable ferrous and ferric salts can be used in these edible mixes and ready-to-serve beverages. In addition to these highly bioavailable ferrous and ferric salts, other sources of bioavailable iron can be included in the food and beverage compositions of the present disclosure. Other sources of iron particularly suitable for fortifying products included certain iron-sugar-carboxylate complexes.

Zinc compounds which can be used in the disclosed compositions can be in any of the commonly used forms such as, e.g., zinc sulfate, zinc chloride, zinc acetate, zinc gluconate, zinc ascorbate, zinc citrate, zinc aspartate, zinc picolinate, amino acid chelated zinc, and zinc oxide.

In some examples, food and beverage compositions can also include one or more dietary fibers. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

Beverage acidity can be adjusted to and maintained within the requisite range by known and conventional methods, e.g., the use of food grade acid buffers. Typically, beverage acidity within the above recited ranges is a balance between maximum acidity for microbial inhibition and optimum acidity for the desired beverage flavor. In some examples, the beverage compositions has a pH of from about 2 to about 8, such as from about 2 to about 4.5 or about 2.7 to about 4.2.

Organic as well as inorganic edible acids may be used to adjust the pH of the beverage composition. The acids can be present in their undissociated form or, alternatively, as their respective salts, for example, potassium or sodium hydrogen phosphate, potassium or sodium dihydrogen phosphate salts. In some examples, the acids include citric acid, malic acid, fumaric acid, adipic acid, phosphoric acid, gluconic acid, tartaric acid, ascorbic acid, acetic acid, phosphoric acid, pyruvic acid or mixtures thereof. The acidulant can also serve as an antioxidant to stabilize beverage components. Examples of commonly used antioxidant include but are not limited to ascorbic acid, EDTA (ethylenediaminetetraacetic acid), and salts thereof.

D. Methods of making muscadine compositions with antioxidant activity

Methods of making muscadine pomace extract compositions with antioxidant activity are also disclosed. The present compositions can be made according to methods that are well known by the ordinarily skilled artisan. In general, the compositions can be prepared by dissolving, dispersing, or otherwise mixing all components singularly or in suitable combinations together and in water where appropriate, agitating with a mechanical stirrer until all of the ingredients have been solubilized or adequately dispersed. Where appropriate, all separate solutions may be combined. Where a shelf stable composition is desired, the final mixture can optionally, be pasteurized or filled aseptically under appropriate process conditions.

These methods can include combining a muscadine (*Vitis rotundifolia*) pomace extract having a polyphenol content of at least 2% and resveratrol from a source other than muscadine with a minimum purity of at least 5% (such as at least 10%, at least 20%, at least 30%, at least 40%, at least 50%, at least 60%, at least 70%, at least 80%, at least 90%, at least 95%, at least 98% or at least 99%) wherein a ratio of muscadine polyphenols to trans-resveratrol is in the range of 0.1/1 to 10/1 (weight to weight), thereby producing a muscadine pomace extract and trans-resveratrol mixture with antioxidant activity. The disclosed methods can further include preparing the muscadine pomace extract prior to combining the muscadine pomace extract with trans-resveratrol.

In one particular example, preparing the muscadine pomace extract includes combining a bronze muscadine pomace extract with a purple muscadine pomace extract. In other examples, preparing the muscadine pomace extract includes extracting a mixture of bronze muscadine pomace and purple muscadine pomace simultaneously. In certain examples, the muscadine pomace extract included within the disclosed compositions is prepared according to the methods disclosed herein. However, it is contemplated that the muscadine pomace extract can be prepared according to known methods in the art including, through crushing, pressing, extraction, filtering (several times), and concentration of the extract by vacuum evaporation followed by freezing. In one example, only water is utilized for the extraction process and no additional components, for example, solvents, carriers, or preservatives, are added to the extract itself. The process is performed under conditions to preserve the polyphenolic compounds while reducing the presence of other molecules, for example, the majority of sugars. In other examples, ethanol or a mixture of ethanol and water are utilized for the extraction process. In particular examples, the extraction process can further include the use of enzymes for clarifying or facilitating extraction. For example, a blend of enzymes from *Aspergillus niger* or pectinase can be used for these purposes. Commercial examples include Scottzyme KS and ScottzymePEC5L from Scott Laboratories.

In other examples, the disclosed compositions are prepared by utilizing muscadine pomace extracts with a total phenol concentration of at least 2%. For example, commercially available muscadine extracts with a total phenol concentration of at least 2% can be used to prepare the disclosed compositions with antioxidant activity.

In a particular example, the methods of preparing a composition with antioxidant activity can further include combining a muscadine pomace extract and resveratrol with an elderberry extract, a purple carrot extract, an excipient (such as glycerin, sorbitol, colloidal silicon dioxide, or a natural flavoring additive) or a combination thereof. In a particular example, the method includes combining a muscadine pomace extract (containing about 4% to about 5% polyphenol content) at 23% to 32% of the total composition with trans-resveratrol at 1.2% to 3.0% of total, a purple carrot extract at 0.12% to 0.20% of total, an elderberry extract at 0.4% to 0.6% of total, sorbitol at 50% to 61% of total, a 99.7% glycerin composition at 8% to 12% of total, and colloidal silicon dioxide at 1% to 2% of total.

In a more particular example, the composition includes combining a muscadine pomace extract (containing 4.1% polyphenol content) at about 28.9% of total with resveratrol at about 1.65% of total, purple carrot extract at about 0.16% of total, elderberry extract at about 0.48% of total, sorbitol at about 54.8% of total, 99.7% glycerin composition at about 10% of total, colloidal silicon dioxide at about 2% of total, Concord grape extract at about 1.27%, Cabernet grape extract at about 0.16% and red grape powder at about 0.48%.

In another more particular example, the composition includes combining a muscadine pomace liquid extract (containing 5% polyphenol content) at about 23.77% of total with trans-resveratrol at about 1.65% of total, purple carrot extract at about 0.16% of total, elderberry extract at about 0.48% of total, sorbitol at about 60.05% of total, 99.7% glycerin composition at about 10% of total, colloidal silicon dioxide at about 2% of total, Concord grape extract at about 1.27%, Cabernet grape extract at about 0.16% and red grape powder at about 0.48%.

In making a ready-to-drink composition, a beverage concentrate may optionally be formed first. One method to prepare the concentrate form of the beverage composition is to start with less than the required volume of water that is used in the preparation of the beverage composition. Another method is to partially dehydrate the finally prepared beverage compositions to remove only a portion of the water and any other volatile liquids present. Dehydration can be accomplished in accordance with well known procedures, such as evaporation under vacuum. The concentrate can be in the form of a relatively thick liquid. A syrup is typically formed by adding suitable ingredients such as electrolytes or emulsions to the beverage concentrate. The syrup is then mixed with water to form a finished beverage or finished beverage concentrate.

Essentially dry mixtures of the disclosed compositions can be prepared by blending the proper amounts and ratios of all the required dry ingredients together. Alternatively, the finally prepared beverage compositions can be dehydrated to give the essentially dry mixture of the beverage composition. The essentially dry mixture, either as, for example, a powder, granules or tablets, can later be dissolved in a proper amount of water, carbonated or non-carbonated, to make the final drinkable beverage or taken in conjunction with water.

As a form of foods, the disclosed compositions can be formulated to any optional form, for example, a granule state, a grain state, a paste state, a gel state, a solid state, or a liquid state. In these forms, various additional substances can be included, such as a binder, a disintegrant, a thickener, a dispersant, a reabsorption promoting agent, a tasting agent, a buffer, a surfactant, a dissolution aid, a preservative, an emulsifier, an isotonicity agent, a stabilizer or a pH controller. In particular examples, when the disclosed compositions are utilized as foods for preservation of health (including, but not limited to improving skin quality), functional foods, etc., it is preferred to contain the active ingredients of the present compositions and extracts (e.g., muscadine pomace extract, resveratrol, purple carrot extract and elderberry extract) in such an amount that the predetermined effects of the present disclosure are shown to be sufficient to provide antioxidant activity.

E. Methods and kits for inhibiting (for example preventing) cellular aging

It is shown herein that the disclosed compositions have improved lipophilic antioxidant activity. It is known that oxidative stress is a central mechanism underlying normal aging. It is also known that lipophilic antioxidants are capable of inhibiting various types of skin damage. Based on these observations, methods of inhibiting cellular aging, such as inhibiting or reducing free radical production or activity, are disclosed. In one example, the method includes administering to a subject in need thereof a dose of a disclosed composition with antioxidant activity sufficient to inhibit or reduce one or more processes associated with cellular aging. For example, inhibiting one or more processes associated with cellular aging includes reducing or inhibiting free radical formation or activity in the subject that ingests the composition.

In some disclosed embodiments, the method includes administering a composition that is ingestible, such as those described herein, that includes a muscadine (*Vitis rotundifolia*) pomace extract derived from bronze muscadine pomace and purple muscadine pomace. In some embodiments, the ratio of bronze muscadine pomace extract to purple muscadine pomace extract in the muscadine pomace extract ranges from 0.1 to 10 (weight to weight), such as from 0.3 to 3 (weight to weight). For example, the ratio of bronze muscadine pomace extract to purple muscadine pomace extract is about 2.75 to about 1 (weight to weight), 2.5 to about 1 (weight to weight), about 2.25 to about 1 (weight to weight), about 2 to about 1 (weight to weight), about 1.5 to about 1 (weight to weight), or about 1 to about 1 (weight to weight). As used herein the term "about" is defined as ±0.5. In a particular example, the ratio of bronze muscadine pomace extract to purple muscadine pomace extract is about 2.25 to about 1 (weight to weight).

In certain embodiments, the orally administered muscadine (*Vitis rotundifolia*) pomace extract has a polyphenol content of at least 2%. For example, the polyphenol content is at least 3%, at least 3.5%, at least 4%, at least 4.5%, at least 5%, at least 6%, at least 8%, at least 10%, at least 12%, or at least 14%. In a particular example, the muscadine (*Vitis rotundifolia*) pomace extract has a polyphenol content of about 4%.

In some embodiments, the method includes administering a composition that is ingestible that includes a muscadine pomace extract as well as other additional ingredients, including but not limited to resveratrol. In some examples, the method includes administering an oral composition that has a ratio of muscadine polyphenols to resveratrol of about 0.75 to 1 (weight to weight). In other examples, the method includes administering a composition including at least a muscadine pomace extract (containing from 2% to 14%, such as 4%, 6%, 8%, 10% or 12% muscadine polyphenols on a liquid weight basis) at 8% to 60% of the total composition muscadine pomace extract and trans-resveratrol at 1.2% to 3.0% of total.

In a further embodiment, the method includes administering an oral composition that includes a muscadine pomace extract having a polyphenol content of at least 2% and resveratrol from a source other than muscadine (such as a Japanese knotweed root extract) with a minimum purity of at least 5%, wherein a ratio of muscadine polyphenols to trans-resveratrol is in the range of 0.1/1 to 10/1 (weight to weight), thereby providing a composition with antioxidant activity sufficient to inhibit or reduce one or more processes associated with cellular aging (including, but not limited to improving skin quality). In a particular example, the method includes administering a composition including a muscadine (*Vitis rotundifolia*) pomace extract having a polyphenol content of at least 2% and resveratrol from a source other than muscadine (such as a Japanese knotweed root extract) with a minimum purity of at least 5%, wherein a ratio of muscadine pomace extract to resveratrol is in the range of 0.2/1 to 50/1 (weight to weight), such as 5/1 to 50/1 (weight to weight) or 20/1 to 50/1 (weight to weight), thereby providing a composition with antioxidant activity. In some examples, the composition has a total ORAC of at least 24 μmole Trolox Equivalents per mg polyphenol (μmoleTE/mg polyphenol).

In other embodiments, the methods improving skin quality by inhibiting or reducing free radical formation or activity in a skin cell by applying a solution or topical ointment containing a muscadine pomace extract either alone or in combination with additional active ingredients, including, but not limited to resveratrol. In one example, the solution or topical ointment includes a disclosed muscadine pomace extract without resveratrol. In another example, the solution or topical ointment includes both a disclosed muscadine pomace extract and resveratrol, such as a muscadine pomace extract including a muscadine polyphenol concentration so that the ratio of muscadine polyphenols to resveratrol is about 0.75 to 1 (weight to weight). The method can be performed by a clinician or other healthcare provider. The method is also designed for home use. The method can reduce the appearance of skin changes associated with aging, visibly reduce human skin wrinkles, and improve the textural quality of skin. Compositions and kits for improving skin quality are also provided that can include a disclosed composition (including oral or topical) with antioxidant activity or muscadine extract and one or more additional anti-aging compositions, such as one or more additional antioxidants.

Any skin surface (e.g., the epidermis of the skin) can be treated with the using the methods provided herein. Skin surfaces that can be treated include, but are not limited to, periorbits, lips, cheeks, nasolabial folds, forehead, neck, upper lip rhytides, stomach, neck, back, chest, hands, legs, feet, or any combination thereof. In an example, the skin of any facial surface can be treated using the methods provided herein. The method can be applied to any facial area and/or to any body surface area, with other immediate areas of application being the chest and neck. More than one skin surface can be treated during the same treatment period. In particular examples, a liquid or cream form of a disclosed composition or extract is applied substantially evenly across the surface of the skin, forming a layer of the composition or extract on the skin.

The disclosed compositions or extracts can contain additional substances that are customarily used in cosmetics, for example, perfume; antimicrobial agents; antibacterial agents; refatting agents; complexing and sequestering agents; pearlescent agents; plant extracts; vitamins, such as retinol or vitamin C; active agents; preservatives; bactericides; surfactants, dyes, colorants, pigments, or any substances which have a coloring effect; emulsifiers; thickeners; softening, moisturizing, and/or humectant substances; or other common constituents of a cosmetic or dermatological formulation, such as alcohols, polyols, polymers, foam stabilizers, electrolytes, organic solvents, or silicone derivatives. The compositions can also comprise functional additives such as keratolytic agents, oxidizers, sun-protection agents, and skin smoothing agents. The compositions may also contain components that are considered beneficial in mesotherapy injectional treatment of the skin and underlying subcutaneous tissue, including antioxidants, such as dimethylaminoethanol, alpha lipoic acid, and ascorbic acid. Agents that may enhance the efficacy of the compositions or extracts, such as lipophilic and lipophobic penetration enhancers (e.g., triethyl citrate, propylene glycol, fatty acid esters and others) may also be included in the compositions. Agents that may enhance the vascular perfusion of the skin, such as aminophyllin, or pentoxifylline may also be included in the compositions. Agents that may enhance the turgor and tonicity of the skin as well as allow for the contraction or shrinkage of the underlying subcutaneous tissue structure, such as phosphatidyl choline and deoxycholate sulfate may also be included in the compositions. Physiologic substances that may provide hormonal benefit, such as substances of estrogenic or testosterrogenic stimulus to the skin, including estriol, and testosterone may also be included in the compositions.

The disclosed muscadine compositions can include one or more preservatives. These preservatives include, for example, Opthiphen™ (from International Specialty Products), Geogard®Ultra (from Lonza), preservatives listed in the European Union Cosmetic Directive and others, such as formaldehyde donors (such as, for example, DMDM hydatoin, which is available under the trade name GLYDAN® from Lonza), iodopropyl butylcarbamates (for example, those which are available under the trade names GLYCACIL-STM from LONZA™ and/or DEKABEN LMB™ from Jan Dekker), parabens (for example, alkyl esters of the p-hydroxybenzoic acid, such as methyl-, ethyl-, propyl-, and/or butylparaben), phenoxyethanol, ethanol, benzoic acid, and salicylic acid. The preservation system can further include preservative auxiliaries, such as octoxyglycerin or glycine soya. Other preservatives or preservative auxiliaries include dibromocyanobutane (2-bromo-2-bromomethylglutarodinitrile), 3-iodo-2-propynyl butylcarbamate, 2-bromo-2-nitropropane-1,3-diol, imidazolidinyl urea, 5-chloro-2-methyl-4-isothiazolin-3-one, 2-chloroacetamide, benzalkonium chloride, and benzyl alcohol.

The compositions can also include one or more conditioners, such as a water soluble conditioning agent. Other conditioners include, for example, compounds that are called polyquaternium in accordance with the International Nomenclature for Cosmetic Ingredients (INCI), in particular Polyquaternium-1 to Polyquaternium-56.

The compositions can be dispensed from a soft tube, a jar, a bottle, a pump, a can, a spray can or spray bottle, or from some other known container.

Musacadine pomace extract composition and kits for improving skin quality are also disclosed herein for use in the home or by a clinician. In one example, this kit is suitable for use by a clinician or aesthetician. In such example, the kit can further include applicators to assist with applying the composition. Generally the kit also includes instructions for use. These instructions can be written or in a digital formal (such as a videotape, DVD or CD) for use with electronic devices such as computers, CD players, mp3 players or DVD players and the like. In another example, the kit is suitable for use in the home. This kit can include an applicator, such as a sponge or cloth, for applying the composition. Alternatively, one or more fingers can be used to apply the composition. Generally, the kit also includes instructions for use. These instructions can be written or in a digital format (such as a videotape, DVD or CD) for use with electronic devices such as computers, CD players, mp3 players or DVD players.

In some examples, the kit includes one of the disclosed compositions or extracts and one or more additional anti-aging compounds, such as another antioxidant (e.g., vitamin C, vitamin E, selenium and/or beta-carotene), either in two separate containers or as a single composition in a single container. In one example, the composition or extract is applied to a target skin area. In one specific non-limiting example, the muscadine pomace extract anti-aging kit can be used by a person in the home as follows. First, a measured quantity of the composition or extract is applied to the surface the skin by the use of an applicator, such as a sponge or cloth, or by the use of one or more fingers, to provide an even layer of the composition or extract on the skin surface. The composition or extract is either allowed a certain time length to be passively absorbed into the skin surface or absorption of the composition/extract by the skin surface can be facilitated by gently rubbing the composition into the skin surface with the fingertips. Generally, normal skin care procedures, such as makeup application and applying additional moisturizing agents, can be resumed following application of the muscadine pomace composition/extract.

This process can be performed as described twice daily, daily, every other day, bi-weekly, weekly, every other week, or monthly, or for some other interval, such as once every 3 to 5 days. Improving skin quality includes reversing, slowing the progression of, or preventing skin changes associated with natural or innate aging. As used herein, prevent and variations thereof refer to any degree of delaying the onset of skin changes. For example, improving skin quality includes the reversal, slowing the progression of, or prevention of skin changes associated with free radical formation and activity. In one example, improving skin quality includes reversal, slowing the progression of, or prevention of skin changes associated with sun damage or photo aging—skin changes associated with exposure to sunlight or other forms of actinic radiation (for example, UV radiation and tanning booths). As another example, improving skin quality also can include reversing, slowing the progression of, or preventing skin changes resulting from extrinsic factors, including, but not limited to, radiation, air pollution, wind, cold, dampness, heat, chemicals, smoke, cigarette smoking, and combinations thereof. Improving skin quality also can include reversing, preventing or reducing scarring that can result, for example, from certain skin conditions (for example, acne), infections (for example, leishmaniasis), or injury (for example, abrasions, punctures, lacerations, or surgical wounds). Improvements to the skin can also include at least one of the following: making facial lines appear less noticeable, making facial lines and/or wrinkles feel plumped, improving the appearance of suborbital lines and/or periorbital lines, improving the appearance of crow's feet, reducing and/or diminishing the appearance of wrinkles, particularly facial wrinkles on the cheeks, forehead (for example, perpendicular wrinkles between eyes, horizontal wrinkles above the eyes), and/or around the mouth, and particularly deep wrinkles, folds, or creases, improving skin suppleness, reducing and/or eliminating fine and/or deep lines, folds and creases, and smoothing skin. Methods for measuring improved skin quality are known in the art. See, for example, U.S. Pat. Nos. 6,866,856 and 6,682,763.

Skin changes treatable by practicing the methods and using the kits disclosed herein include, for example, wrinkles (including, but not limited to, human facial wrinkles), creases, furrows, folds and fine lines, deepening of skin lines, thinning of skin, preventing or reducing scarring, yellowing of the skin, mottling, hyperpigmentation, appearance of pigmented and/or non-pigmented age spots, leatheriness, loss of elasticity, loss of recoilability, loss of collagen fibers, abnormal changes in the elastic fibers, deterioration of small blood vessels of the dermis, formation of solar increased visible vasculature on the skin surface, and combinations thereof.

Improving skin quality includes decreasing, reducing, and/or minimizing one or more of the skin changes discussed above. Improving skin quality can result in the skin having a more youthful appearance. Improving skin quality can result in the skin having a smoother, hydrated (less dry), or less scaly appearance. For example, in certain embodiments, improving skin quality can include a reduction in roughness, dryness, or scaliness. Improving skin quality includes the effacement and improvement of lines and wrinkles, improvement in turgor, and tonicity, with the observed desired effects of lifting and tightening.

The textural qualities of the skin can be improved, including softness, suppleness, and smoothness, leading to enhancement of luster, clarity and brightness. Additional and important qualities of the skin that can be subjectively and objectively measured include, but are not limited to skin laxity, or conversely skin tightness, and the presence and degree of textural fine lines and coarser lines within the skin.

These are the same qualities by which the external aspects of appearance (for example, aging of skin) are judged. Improvement in these qualities by the method of treatment and kits disclosed herein result in a benefit based on visual judgment of appearance. Changing a quality of the skin by the methods disclosed herein lessens the appearance of aging of the skin.

Desired benefits may include not only physiologic benefit to the skin, but therapeutic and pharmacologic benefits, such as possible malignancy prevention and treatment, whether by chemoprevention or enhancement of photodynamic therapy. Benefits may also include acne treatment and suppression, by including compositions which suppress sebaceous glandular activity F. Pharmaceutical Compositions The disclosed muscadine pomace extracts and compositions can be useful, at least, for the inhibiting (for example preventing) one or more oxidative processes, such as free radical formation associated with cellular events, such as cellular aging. Accordingly, pharmaceutical compositions comprising at least one disclosed muscadine pomace extract either alone or in combination with resveratrol are also described herein.

Formulations for pharmaceutical compositions are well known in the art. For example, *Remington's Pharmaceutical Sciences*, by E. W. Martin, Mack Publishing Co., Easton, Pa., 19th Edition, 1995, describes exemplary formulations (and components thereof) suitable for pharmaceutical delivery of at least one disclosed muscadine pomace extract either alone or in combination with resveratrol. In some examples, the compositions also include additional agents such as purple carrot root extract or elderberry extract. Pharmaceutical compositions comprising at least one of these compounds can be formulated for use in human or veterinary medicine. Particular formulations of a disclosed pharmaceutical composition may depend, for example, on the mode of administration (e.g., oral, topical or parenteral) and/or on the condition to be treated (e.g., free radical production or activity). In some embodiments, formulations include a pharmaceutically acceptable carrier in addition to at least one active ingredient, such as a muscadine pomace extract.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions such as powder, pill, tablet, or capsule forms conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin.

The disclosed pharmaceutical compositions may be formulated as a pharmaceutically acceptable salt. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydriodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in *Remington's Pharmaceutical Sciences*, 19th Edition, Mack Publishing Company, Easton, Pa., 1995. A pharmaceutically acceptable salt may also serve to adjust the osmotic pressure of the composition.

The dosage form of a disclosed pharmaceutical composition will be determined by the mode of administration chosen. For example, oral dosage forms may be employed. Oral formulations may be liquid such as syrups, solutions or suspensions or solid such as powders, pills, tablets, or capsules. Methods of preparing such dosage forms are disclosed herein, or will be apparent, to those skilled in the art.

Certain embodiments of the pharmaceutical compositions comprising a disclosed compound may be formulated in unit dosage form suitable for individual administration of precise dosages. The amount of active ingredient administered will depend on the subject being treated, the severity of the disorder, and the manner of administration, and is known to those skilled in the art. Within these bounds, the formulation to be administered will contain a quantity of the extracts or compounds disclosed herein in an amount effective to achieve the desired effect in the subject being treated. In particular examples, for oral administration the compositions are provided in the form of a liquid containing about 75 mg of muscadine pomace extract polyphenols and 100 mg of trans-resveratrol. In other examples, for oral administration the compositions are provided in the form of a tablet containing from about 1.0 to about 500 mg of the active ingredients, particularly about 10.0 mg, about 50 mg, 100 mg, about 150 mg, about 175 mg, about 200 mg, about 210 mg, about 225 mg, about 250 mg, about 300 mg, about 400 mg or about 500 mg of the active ingredient for the symptomatic adjustment of the dosage to the subject being treated. In one exemplary oral dosage regimen, a tablet containing from about 1 mg to about 500 mg (such as about 150 mg to about 225 mg) active ingredient is administered at least once daily. In other examples, a tablet containing from about 1 mg to about 500 mg (such as about 150 mg to about 225 mg) active ingredient is administered at least once a week, such as at least two times, at three times, at least four times, at least five times, or at least six times a week or daily.

G. Administration of Disclosed Extracts and Compositions

Methods of administration of any of the disclosed compositions and extracts are routine. For example, the disclosed methods (such as those that include a composition with antioxidant activity for preventing or reducing one or more processes associated with aging) can be administered via injection, intratumorally, orally, topically, transdermally, parenterally, or via inhalation or spray. In a particular example, a composition is administered orally to a mammalian subject, such as a human, in the form of a non-beverage food, a beverage or a dietary supplement. In another example, a composition is administered topically to a skin surface of a mammalian subject, such as a human.

The therapeutically effective amount of the agents administered can vary depending upon the desired effects and the subject to be treated. In one example, the method includes daily administration of at least 1 mg of the composition to the subject (such as a human subject). For example, a human can be administered at least 1 g or at least 10 g of the composition daily, such as 1 g to 5 g daily, 5 g to 10 g daily, for example 7 g daily. In one example, the subject is administered at least 5 g of the composition including muscadine pomace extract and resveratrol. In other examples, the subject is administered at least 6.3 g orally of such composition. The dosage can be administered in divided doses (such as 2, 3, or 4 divided doses per day), or in a single dosage daily.

In particular examples, the subject is administered the therapeutic composition (such as a disclosed anti-aging supplement that includes resveratrol and muscadine extract) on a multiple daily dosing schedule, such as at least two consecutive days, 10 consecutive days, and so forth, for example for a period of weeks, months, or years. In one example, the subject is administered the therapeutic composition (such as a disclosed anti-aging supplement that includes resveratrol and muscadine extract) that includes daily for a period of at least 30 days, such as at least 2 months, at least 4 months, at least 6 months, at least 12 months, at least 24 months, or at least 36 months.

The therapeutic compositions, such as a disclosed anti-aging supplement that includes trans-resveratrol and muscadine pomace extract or a muscadine pomace extract alone, can further include one or more biologically active or inactive compounds (or both), such as additional antioxidant agents and conventional non-toxic pharmaceutically acceptable carriers, respectively. In a particular example, a therapeutic composition further includes one or more biologically inactive compounds. Examples of such biologically inactive compounds include, but are not limited to: carriers, thickeners, diluents, buffers, preservatives, and carriers. The pharmaceutically acceptable carriers useful for these formulations are conventional (see *Remington's Pharmaceutical Sciences*, by E. W. Martin, Mack Publishing Co., Easton, Pa., 19th Edition (1995)). In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can include minor amounts of non-toxic auxiliary substances, such as wetting or emulsifying agents, preservatives, and pH buffering agents and the like, for example sodium acetate or sorbitan monolaurate.

Although the present disclosure has provided a detailed description using any of the disclosed compositions and extracts for preventing or inhibiting one or more processes associated with cellular aging, it is contemplated the disclosed compositions and extracts can be used not only as an antioxidant to prevent or inhibit one or more processes associated with cellular aging, but to treat any disorder associated with oxidative stress. For example, it is contemplated that the present extracts and compositions can be used to reduce, prevent or treat oxidative stress associated with the pathogenesis of chronic inflammatory diseases such as diabetes, cancer, atherosclerosis and other cardiovascular disease as well as with degenerative diseases such as Alzheimer's disease and Parkinson's disease.

The subject matter of the present disclosure is further illustrated by the following non-limiting Examples.

EXAMPLES

Example 1

Determination of Ellagic Acid Solubility in Muscadine Pomace Extracts

This example illustrates the effects of various ratios of bronze to purple pomace extracts on ellagic acid solubility.

Separate fermented bronze and purple pomace extracts were heated and then mixed in the ratios provided in Table 1 at a total volume of 100 mls.

TABLE 1

Various Ratios of Bronze/Purple Pomace extracts at 1X concentration

| Bronze (mls) | Purple (mls) |
|---|---|
| 75 | 25 |
| 65 | 35 |
| 50 | 50 |
| 25 | 75 |

The resulting extract mixtures were at a 1× concentration since no concentration of the separate bronze and purple pomace extracts had taken place. A 1× concentration typically contained about a 2% solids solution (100 grams of solution equal to 2 grams of dry extract). Approximately 20 milliliters of each ratio was transferred into a respective glass test tube and capped with foil. Samples were heated for 30 minutes at 85° C., then removed from the heat source and allowed to come to room temperature. Samples were then filtered through 0.45 µm PTFE filter w/GMP and analyzed via HPLC/MS to determine their content of ellagic acid. Separate bronze and purple muscadine pomace extracts were also analyzed, through the same process, to determine the baseline values of ellagic acid in both the bronze and purple pomace extracts and to determine the content of anthocyanins in the purple pomace extract. The total area of ellagic acid in the samples was then determined by reverse phase HPLC with a UV-VIS detection at 254 nm in tandem with a Ion-Trap mass detector, using extracted ion chromatogram (EIC) at $[M-H]^- = 301$ amu.

To prepare various ratios of bronze/purple pomace extracts at 40% solids, separate bronze and purple muscadine pomace extracts at 1× were dried down into a powder form and reconstituted in water to produce a liquid containing 40% solids. These two separate solutions were then mixed into various ratios according to weight (wt) rather than volume. The various ratios evaluated are provided in Table 2A and 2B.

TABLE 2A

Determination of ellagic acid solubility in various Bronze/Purple extract ratios at 1X concentration.

| | Pre-Analysis Conditions (non-filtered) Heat Extract @ 85° C./30 mins. Allow Cool R.T. (1 hour)/Filter/Analyze | | | % Increase Ellagic Acid Relative µg/ml |
|---|---|---|---|---|
| Sample ID | Ellagic Acid Relative µg/ml Experimental | Ellagic Acid Relative µg/ml Expected | Anthocyins Relative µg/ml Extrapolated | Experimental vs. Expected |
| Bronze Extract @ 1X | 29.53 | | | |
| Purple Extract @ 1X) | 77.81 | | 472.50 | |
| 25:75 Purple/Bronze Ratio @ 1X | 43.43 | 41.60 | 118.12 | 4.40 |
| 35:65 Purple/Bronze Ratio @ 1X | 51.11 | 46.43 | 165.37 | 10.07 |
| 50:50 Purple/Bronze Ratio @ 1X | 58.59 | 53.67 | 236.25 | 9.16 |
| 75:25 Purple/Bronze Ratio @ 1X | 72.23 | 65.74 | 354.37 | 9.87 |

TABLE 2B

Determination of ellagic acid solubility in various Bronze/Purple extract ratios at approximately 20X concentration or 40% solids level.

| | Pre-Analysis Conditions (non-filtered) Heat Extract @ 85° C./30 mins. Allow Cool R.T. (1 hour)/Filter/Analyze | | | % Increase Ellagic Acid Relative ug/ml |
|---|---|---|---|---|
| Sample ID | Ellagic Acid Relative ug/ml Experimental | Ellagic Acid Relative ug/ml Expected | Anthocyanins Relative ug/ml Extrapolated | Experimental vs. Expected |
| Bronze Extract @ ~40% solids | 3.00 | | | |
| Purple Extract @ ~40% solids | 26.25 | | 981.42 | |
| 2.25:1 Bronze/Purple Ratio ~40% solids | 12.19 | 10.15 | 301.97 | 20.13 |

TABLE 2B-continued

Determination of ellagic acid solubility in various Bronze/Purple extract ratios at approximately 20X concentration or 40% solids level.

| Sample ID | Pre-Analysis Conditions (non-filtered) Heat Extract @ 85° C./30 mins. Allow Cool R.T. (1 hour)/Filter/Analyze | | | % Increase Ellagic Acid Relative ug/ml |
|---|---|---|---|---|
| | Ellagic Acid Relative ug/ml Experimental | Ellagic Acid Relative ug/ml Expected | Anthocyanins Relative ug/ml Extrapolated | Experimental vs. Expected |
| 2:1 Bronze/Purple Ratio ~40% solids | 13.29 | 10.75 | 327.14 | 23.66 |
| 1:1 Bronze/Purple Ratio ~40% solids | 20.01 | 14.62 | 490.71 | 36.80 |

Approximately 10 milliliters of each ratio was transferred into a respective glass test tube and capped with foil. Samples were heated for 30 minutes at 85° C., then removed from the heat source and allowed to come to room temperature. Samples were then filtered through a 0.45 μm PTFE filter w/GMP and analyzed via HPLC/MS to determine their content of ellagic acid. Separate bronze and purple muscadine pomace extracts were also analyzed, through the same process, to determine the baseline values of ellagic acid in both bronze and purple muscadine pomace extracts and to determine the content of anthocyanins in the purple muscadine pomace extract. Validated test method C2505 was used to determine the total area of ellagic acid in the samples, in tandem with a Ion-Trap mass detector using extracted ion chromatogram (EIC) at $[M-H]^- = 301$ amu.

These studies found that a ratio of 65% to 35% bronze to purple pomace extract (volume to volume) was sufficient to promote the maximum solubility of ellagic acid in a mixture of the two pomace extracts at the 1× concentration level. Further, at a 40% solids level, the solubility of ellagic acid continued to increase as the content of purple muscadine pomace extract increased in the mixture. These findings suggest that at a 40% solids level, greater amounts of ellagic acid existed in the solid form, so a higher content of purple pomace extract is required to fully solubilize all the ellagic acid present in the mixture. These studies may also suggest that anthocyanins contained in the purple muscadine pomace extract influence the solubility of ellagic acid contained within the bronze muscadine pomace extract.

Example 2

Anti-aging Dietary Supplement and Preparation thereof

This example provides dietary supplements that can be consumed to prevent or inhibit one or more processes associated with cellular aging.

The disclosed anti-aging dietary supplements were prepared according to the formula provided in Table 3a or Table 3b.

TABLE 3A

Anti-aging Dietary Supplement

| Raw Material | Formula (mg/dose or serving) | % Formula |
|---|---|---|
| Resveratrol 98% | 104.082 | 1.649% |
| Muscadine pomace liquid extract containing 4.1% polyphenol content extract | 1829.268 | 28.990% |
| Glycerin 97% | 631.000 | 10.000% |
| Colloidal silicon dioxide | 126.00 | 1.997% |
| Flavor (Concord grape extract) | 80.00 | 1.268% |
| Flavor (Cabernet grape extract) | 10.00 | 0.158% |
| Elderberry extract | 30.00 | 0.475% |
| Red Grape powder (T-1000) | 30.00 | 0.475% |
| Sorbitol | 3459.650 | 54.828% |
| Purple Carrot Extract | 10.00 | 0.158% |
| Totals: | 6310 | 100% |

TABLE 3B

Anti-aging Dietary Supplement

| Raw Material | Formula (mg/dose or serving) | % Formula |
|---|---|---|
| Resveratrol 98% | 104.082 | 1.649% |
| Muscadine pomace liquid extract containing 5% polyphenol content extract | 1500.00 | 23.772% |
| Glycerin 97% | 631.000 | 10.000% |
| Colloidal silicon dioxide | 126.00 | 1.997% |
| Flavor (Concord grape extract) | 80.00 | 1.268% |
| Flavor (Cabernet grape extract) | 10.00 | 0.158% |
| Elderberry extract | 30.00 | 0.475% |
| Red Grape powder (T-1000) | 30.00 | 0.475% |
| Sorbitol | 3788.918 | 60.046% |
| Purple Carrot Extract | 10.00 | 0.158% |
| Totals: | 6310 | 100% |

The dietary supplement includes instructions regarding dosages. The instructions indicate that 5 milliliters of the supplement (approximately one teaspoon) can be taken daily before a meal and used as an anti-aging supplement, for example, for inhibiting one or more processes associated with cellular aging.

Example 3

Antioxidant Capacity of Muscadine Pomace Extract and Japanese Knotweed Root Extract Mixture and Anti-aging Supplement This example demonstrates the improved antioxidant capacity of a mixture and supplement containing a Japanese knotweed extract and muscadine pomace extracts as measured by an Oxygen Radical Absorbance Capacity (ORAC) assay.

The antioxidant capacity of two botanical extracts separately or in combination in a mixture or supplement was evaluated using the ORAC assay. This assay has been used to measure the antioxidant capacity of a wide range of foods and beverages and is the basis for the data contained in the USDA ORAC database. Both hydrophilic antioxidant capacity and lipohilic antioxidant capacity can be measured by this test.

The following samples were analyzed: (1) Dried/powdered Japanese knotweed root extract standardized to a minimum 98% trans-resveratrol (actual content was 100% trans-resveratrol); (2) Dried/powdered Muscadine pomace extract (2:1 ratio of bronze to purple pomace) containing 14.4% total polyphenol content; (3) Mixture of the above dried/powdered Japanese knotweed and dried/powdered muscadine pomace extracts in a 1:5.36 (wt:wt) ratio (total polyphenol content was 27.5% of mixture and the ratio of muscadine polyphenols to trans-resveratrol was 0.75 to 1); and (4) Anti-aging supplement provided in Example 2, Table 3a. Hydrophilic, lipophilic and total ORAC values were measured (total ORAC value is the sum of the hydrophilic and lipophilic values) and the results are expressed as μmole Trolox Equivalents per milligram polyphenol (μmoleTE/mg polyphenol). The results are shown in Table 4.

TABLE 4

Hydrophilic, lipophilic and total ORAC values for Samples 1-4 as expressed as μmoleTE/mg polyphenol.

| Sample Extract | ORAC$_{hydrophilic}$ | ORAC$_{lipophilic}$ | ORAC$_{total}$ |
|---|---|---|---|
| (1) Japanese knotweed | 29.85 | 1.46 | 31.31 |
| (2) Muscadine pomace | 9.69 | 0.06 | 9.74 |
| (3) Mixture - predicted additivity | 21.19 | 0.86 | 22.05 |
| (3) Mixture - actual value | 21.83 | 4.35 | 26.18 |
| (4) Anti-aging supplement provided in Table 3a- predicted additivity | 17.67 | 0.72 | 18.39 |
| (4) Anti-aging supplement provided in Table 3a - actual value | 22.12 | 1.92 | 24.04 |

As displayed in Table 4, the measured hydrophilic ORAC value of the mixture is similar to the predicted value based on the additive effects of the two extracts. However, the measured lipophilic ORAC value of the mixture is five times greater than the predicted additive value resulting in a 20% increase in the total ORAC value. A similar synergy was observed for the composition, having close to three times the predicted ORAC score based on additivity. Table 5 shows the results expressed as ORAC value per gram of material (vs per mg polyphenol as shown in Table 4). As displayed in Table 5, the synergistic effects of the muscadine pomace extract and Japanese knotweed root extract mixture and the anti-aging supplement in producing lipophilic antioxidant capacity are maintained when values are expressed as ORAC per gram of material:

TABLE 5

Hydrophilic, lipophilic and total ORAC values for Samples 1-4 as expressed as ORAC value per gram of material.

| Extract Sample | ORAC$_{hydrophilic}$ | ORAC$_{lipophilic}$ | ORAC$_{total}$ |
|---|---|---|---|
| (1) Japanese knotweed | 29,852 | 1,457 | 31,309 |
| (2) Muscadine pomace | 1,356 | 8 | 1,364 |
| (3) Mixture - predicted additivity | 5,830 | 236 | 6065 |
| (3) Mixture - actual value | 6,003 | 1,197 | 7200 |
| (4) Anti-aging Supplement provided in Table 3a - predicted additivity | 588.33 | 23.85 | 612.07 |
| (4) Anti-aging Supplement provided in Table 3a - actual value | 736 | 64 | 800 |

These studies demonstrated a strong synergistic effect of the muscadine pomace extract and Japanese knotweed root extract mixture and anti-aging supplement in producing lipophilic antioxidant capacity. The selective synergy exhibited in the lipophilic conditions was unexpected. Therefore, the present findings demonstrate the improved antioxidant capacity of a mixture containing a Japanese knotweed extract and a muscadine pomace extract as measured by the ORAC assay when compared to the either of the extracts alone.

Example 4

Antioxidant Capsule Formulation and Preparation

This example provides an antioxidant capsule formulation and preparation thereof, that can be used to inhibit one or more oxidative processes, including preventing or inhibiting free radical formation.

An aqueous extract of a 2:1 ratio of bronze to purple pomace having a solids content of 40% and a polyphenol content, measured as Gallic Acid equivalents (GAEs), of 10% on a solids basis was treated as follows: 1.33 Kg of maltodextrin MD 100 was added to 10Kg of the above referenced pomace concentrate. The mixture was blended to dissolve the maltodextrin. Subsequently, this liquid concentrate was freeze dried to generate a dry material. Chemical values of the dried muscadine/maltodextrin material was as follows: (1) total polyphenols (as %GAEs), NLT 7.0% (dry basis); gallic acid (HPLC), NLT 0.3% (dry basis) and free ellagic acid (HPLC), NLT 0.15% (dry basis). Characteristics of the dried muscadine/maltodextrin are provided in Table 6.

TABLE 6

Characteristics of the dried Muscadine/Maltodextrin material.

| | |
|---|---|
| Appearance: | Reddish purple powder |
| Flavor: | characteristic of grape extract |
| Odor: | characteristic of grape extract |

Capsules were prepared by weighing out batch quantities of the individual raw materials. The raw materials were passed through a Comil® milling machine, sending the maltodextrin through the mill last. The milled materials were blended until homogenous and then filled into size "0" two piece capsules on an encapsulator. An example of the dosage form manufactured is provided in Table 7 and muscadine/resveratrol capsule analysis results are provided in Table 8.

TABLE 7

Dosage form manufactured - 3 capsules/dose

| Raw Material | claim/dose | Overage | RM assay | mg/dose | mg/cap |
|---|---|---|---|---|---|
| Muscadine/MD100 | 75 mg | 10% | 75 mg/gm | 1100 | 366.67 |
| Trans-Resveratrol | 100 mg | 10% | 98% | 112.245 | 37.415 |
| Microcrystalline | | | | 195 | 65.0 |
| Cabosil | | | | 25.0 | 8.333 |
| Magnesium | | | | 14.0 | 4.667 |
| Maltodextrin | | | | 203.755 | 67.918 |
| | | | Totals | 1650 | 550 |

TABLE 8

Muscadine/resveratrol capsule analysis results.

| Test parameter | Specification (per capsule) | Assay/Result |
|---|---|---|
| Appearance: | size "0" two piece dark purple capsule | Conforms |
| Odor: | characteristic of grape extract | Conforms |
| Capsule dimension: | 0.864"-0.876" | Conforms |
| Gross wt. (10 caps.): | 6.36-6.75 gm | 6.48 gm |
| Fill Wt.: | 0.539-0.578 gm | 0.556 gm |
| Disintegration time: | NMT 45 min | 28 min |
| Polyphenols (as GAEs) | min. 58.3 mg | 61.34 |
| Trans-Resveratrol | min. 33.3 mg | 36.8 |

Example 5

Reduction of Oxidative Stress in Human Subjects

This example demonstrates the in vivo efficacy of the antioxidant capsule described in Example 4 as assessed in a placebo-controlled clinical trial.

The capsules contained a mixture of muscadine pomace extract and Japanese knotweed extract to provide 75 mg of muscadine polyphenols and 100 mg of trans-resveratrol per 3 capsule dose (Tables 7 and 8). It is known that meal consumption acutely increases oxidative stress and produces an inflammatory response. For example, it has been shown that consumption of a 900 kcal fast food meal elicits significant increases in reactive oxygen species (ROS) generation in circulating mononuclear cells (MNC) and polymorphonuclear leukocytes (PMN) in healthy normal weight humans (Aljada et al. *Am. J. Clin. Nutr.* 79:682-690, 2004). These changes are attended by elevated expression in MNC of p47phox protein, a subunit of the enzyme, NADPH oxidase, a mediator of ROS generation.

To test the effects of the antioxidant capsules in this model of postprandial oxidative stress, a group of 10 healthy subjects (age: 37±4 yrs, BMI 22.6±0.5 kg/m2) were given, in two separate days, a 910 kcal fast food meal with either a single dose (3 capsules) of the antioxidant formulation or placebo (3 capsules) taken 10 minutes before the meal. Blood samples were collected at baseline and at 1, 3 and 5 hours following meal intake. Circulating concentrations of glucose, insulin and lipids were similar after each treatment indicating that the disclosed antioxidant capsules did not alter the digestion/absorption of the meal. However, at one hour after meal consumption, the disclosed antioxidant capsule treatment greatly attenuated the increase in ROS generation in both MNC (15% versus 62% for placebo) and PMN (8% versus 64% for placebo). In addition, meal plus placebo intake caused a significant increase in protein levels of p47phox by 148% over the baseline ($P<0.05$) in MNC whereas meal plus antioxidant capsule intake completely prevented any significant change in MNC p47phox levels ($P<0.05$ with 2-way RMANOVA). Moreover, the DNA binding activity of the anti-oxidative stress transcription factor, Nrf-2, was significantly increased by 150% ($P<0.05$ by RMANOVA and 2-way RMANOVA) over the baseline at 3 hours following the meal plus antioxidant capsule intake compared to the placebo treated group wherein there was actually a decline in the DNA binding activity of this protective transcription factor. Nrf-2 binds to the antioxidant response element (ARE) promoter sequence of multiple genes encoding endogenous antioxidant enzymes (e.g., glutathione-S-transferase) and hence, the increased DNA binding of activity of Nrf-2 following intake of the disclosed antioxidant formulation suggests potential for upregulation of multiple cellular defenses.

Finally, following meal and placebo ingestion there was a significant rise in plasma endotoxin levels by 60% over the baseline at 3hr ($P<0.05$) while there was a significant fall in endotoxin concentrations by 28% below the baseline at 1 hour when the meal was consumed with the disclosed antioxidant capsules ($P<0.05$ using RMANOVA and 2-way RMANOVA). Endotoxin is a powerful inflammatory signal that precipitates the activation of a variety of cytokines that increase oxidative stress.

These results demonstrate novel in vivo antioxidant effects of a mixture of muscadine pomace extract and Japanese knotweed (ratio of muscadine polyphenols to trans-resveratrol of 0.75 to 1) and thus extend the in vitro findings of the synergistic antioxidant capacity of this mixture (Example 3).

Based upon these findings, methods of inhibiting oxidative stress are enabled. For example, the disclosed composition is administered to a subject to inhibit oxidative stress, such as that associated with meal consumption. In one example, the disclosed composition is administered 30 minutes before or after eating, such as 10 minutes before or after eating. In a particular example, the composition is administered approximately 10 minutes before eating.

In view of the many possible embodiments to which the principles of the disclosure may be applied, it should be recognized that the illustrated examples are only examples of the disclosed matter and should not be taken as limiting the scope of the disclosure. Rather, the scope of the disclosure is defined by the following claims. We therefore claim as our invention all that comes within the scope and spirit of these claims.

We claim:

1. A muscadine pomace extract composition comprising a liquid bronze muscadine pomace extract combined with a liquid purple muscadine pomace extract to produce a liquid muscadine pomace extract, wherein a) the bronze muscadine pomace extract and the purple muscadine pomace extract are solvent extracts; b) the mixture of bronze muscadine pomace extract and purple muscadine pomace extract promotes solubility of ellagic acid in the muscadine pomace extract; c) the bronze muscadine pomace extract and the purple muscadine pomace extract are filtered and fermented extracts; and d) the muscadine pomace extract composition has a polyphenol content of at least 2%.

2. The muscadine pomace extract composition of claim 1, wherein a ratio of bronze muscadine pomace extract to purple muscadine pomace extract ranges from 0.1 to 10 (weight to weight).

3. The muscadine pomace extract composition of claim 1, wherein the muscadine pomace extract has a total polyphenol content of at least 4%.

4. The composition of claim 1, wherein the composition further comprises an excipient or an additional ingredient.

5. The composition of claim 1, wherein the composition is provided in a non-beverage food, a beverage, or dietary supplement or cosmetic composition.

6. The composition of claim 1, wherein the bronze muscadine pomace extract and purple muscadine pomace extract together comprises 20% to 50% solids in a liquid.

7. The composition of claim 1, further comprising resveratrol from a source other than muscadine pomace.

8. The composition of claim 7, wherein the source of resveratrol other than muscadine pomace is Japanese knotweed extract.

9. A muscadine pomace extract composition comprising
a mixture of a bronze muscadine pomace extract and purple muscadine extract, wherein a) the bronze muscadine pomace extract and purple muscadine pomace extract are liquid solvent extracts that are filtered and fermented extracts, b) a ratio of the bronze muscadine pomace extract to the purple muscadine pomace extract ranges from 0.1 to 10 (weight to weight), and c) the muscadine pomace extract has a polyphenol content of at least 2%.

10. The muscadine pomace extract composition of claim 9, wherein the muscadine pomace extract has a total polyphenol content of at least 4%.

11. The composition of claim 9, wherein the composition further comprises an excipient or an additional ingredient.

12. The composition of claim 9, wherein the composition is provided in a non-beverage food, a beverage, dietary supplement, or cosmetic composition.

13. The composition of claim 9, wherein the bronze muscadine pomace extract and purple muscadine pomace extract together comprises 20% to 50% solids in a liquid.

14. The composition of claim 9, further comprising resveratrol from a source other than muscadine pomace.

15. The composition of claim 14, wherein the resveratrol from the source other than muscadine pomace is Japanese knotweed extract.

16. A muscadine pomace extract composition comprising a filtered and fermented liquid solvent extract from a mixture of bronze muscadine pomace and purple muscadine pomace, wherein the mixture of bronze muscadine pomace and purple muscadine pomace promotes ellagic acid solubility in the liquid solvent extract, and wherein the muscadine pomace extract composition has a polyphenol content of at least 2%.

17. The composition of claim 16, wherein ratio of the bronze muscadine pomace to the purple muscadine pomace ranges from 0.1 to 10 (weight to weight).

18. The composition of claim 16, wherein the composition further comprises an excipient or an additional ingredient.

19. The composition of claim 1, wherein the composition is formulated as a solid.

20. The composition of claim 1, wherein the composition is formulated as a powder, pill, tablet or capsule.

21. The composition of claim 4, wherein the composition is formulated as a solid.

22. The composition of claim 4, wherein the composition is formulated as a powder, pill, tablet or capsule.

23. The composition of claim 7, wherein the composition is formulated as a solid.

24. The composition of claim 7, wherein the composition is formulated as a powder, pill, tablet or capsule.

25. The composition of claim 9, wherein the composition is formulated as a solid.

26. The composition of claim 9, wherein the composition is formulated as a powder, pill, tablet or capsule.

27. The composition of claim 11, wherein the composition is formulated as a solid.

28. The composition of claim 11, wherein the composition is formulated as a powder, pill, tablet or capsule.

29. The composition of claim 14, wherein the composition is formulated as a solid.

30. The composition of claim 14, wherein the composition is formulated as a powder, pill, tablet or capsule.

31. The composition of claim 16, wherein the composition is formulated as a solid.

32. The composition of claim 16, wherein the composition is formulated as a powder, pill, tablet or capsule.

33. The composition of claim 18, wherein the composition is formulated as a solid.

34. The composition of claim 18, wherein the composition is formulated as a powder, pill, tablet or capsule.

\* \* \* \* \*